(12) United States Patent
McVicar

(10) Patent No.: US 9,718,853 B2
(45) Date of Patent: *Aug. 1, 2017

(54) ANHYDROUS POLYMORPHS OF [(2R,3S,4R,5R)-5-(6-(CYCLOPENTYLAMINO)-9H-PURIN-9-YL)-3,4-DIHYDROXYTETRA-HYDROFURAN-2-YL)] METHYL NITRATE AND PROCESSES OF PREPARATION THEREOF

(71) Applicant: Inotek Pharmaceuticals Corporation, Lexington, MA (US)

(72) Inventor: William K. McVicar, Sudbury, MA (US)

(73) Assignee: Inotek Pharmaceuticals Corporation, Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/005,697

(22) Filed: Jan. 25, 2016

(65) Prior Publication Data

US 2016/0137686 A1    May 19, 2016

Related U.S. Application Data

(63) Continuation of application No. 13/750,389, filed on Jan. 25, 2013, now Pat. No. 9,278,991.

(60) Provisional application No. 61/591,037, filed on Jan. 26, 2012.

(51) Int. Cl.
| | |
|---|---|
| *A01N 43/04* | (2006.01) |
| *A61K 31/70* | (2006.01) |
| *C07H 19/20* | (2006.01) |
| *C07H 19/167* | (2006.01) |
| *C07H 19/173* | (2006.01) |
| *C07H 19/16* | (2006.01) |
| *C07H 1/06* | (2006.01) |

(52) U.S. Cl.
CPC .............. *C07H 19/16* (2013.01); *C07H 1/06* (2013.01); *C07H 19/167* (2013.01)

(58) Field of Classification Search
CPC ......... C07H 19/16; C07H 19/167; C07H 1/06
See application file for complete search history.

(56) References Cited

U.S. PATENT DOCUMENTS

| | | | |
|---|---|---|---|
| 3,819,613 A | 6/1974 | Kawazoe et al. |
| 3,832,341 A | 8/1974 | Duschinsky |
| 4,242,505 A | 12/1980 | Kawahara et al. |
| 4,849,311 A | 7/1989 | Itoh et al. |
| 4,968,697 A | 11/1990 | Hutchison |
| 5,140,015 A | 8/1992 | Olsson et al. |
| 5,206,222 A | 4/1993 | Forman et al. |
| 5,219,840 A | 6/1993 | Gadient et al. |
| 5,221,763 A | 6/1993 | Ueno et al. |
| 5,278,150 A | 1/1994 | Olsson et al. |
| 5,280,015 A | 1/1994 | Jacobson et al. |
| 5,296,504 A | 3/1994 | Stjernschantz et al. |
| 5,304,277 A | 4/1994 | Ohara et al. |
| 5,338,430 A | 8/1994 | Parsonage et al. |
| 5,407,793 A | 4/1995 | Del Nido et al. |
| 5,422,368 A | 6/1995 | Stjernschantz et al. |
| 5,443,836 A | 8/1995 | Downey et al. |
| 5,589,467 A | 12/1996 | Lau et al. |
| 5,591,887 A | 1/1997 | Ueno et al. |
| 5,604,210 A | 2/1997 | Nagaoka et al. |
| 5,620,676 A | 4/1997 | Jacobson et al. |
| 5,770,759 A | 6/1998 | Ueno et al. |
| 5,789,416 A | 8/1998 | Lum et al. |

(Continued)

FOREIGN PATENT DOCUMENTS

| | | |
|---|---|---|
| CN | 1164122 A | 11/1997 |
| CN | 101010085 | 8/2007 |

(Continued)

OTHER PUBLICATIONS

Fredholm, Bertil B. et al., "International Union of Pharmacology. XXV. Nomenclature and Classification of Adenosine Receptors," Pharmacological Reviews, vol. 53(4):527-552 (2001).

(Continued)

*Primary Examiner* — Lawrence E Crane
(74) *Attorney, Agent, or Firm* — Nelson Mullins Riley & Scarborough LLP; Jane E. Remillard, Esq.; Cynthia L. Kanik

(57) ABSTRACT

The present invention provides novel anhydrous polymorph forms of [(2R,3S,4R,5R)-5-(6-(cyclopentylamino)-9H-purin-9-yl)-3,4-dihydroxytetrahydrofuran-2-yl)]methyl nitrate (compound A), a selective adenosine $A_1$ receptor agonist with a number of therapeutic uses including the treatment of elevated intra-ocular pressure. Also provided are methods for the preparation of the anhydrous polymorphic forms of compound A, pharmaceutical compositions and methods of treatment.

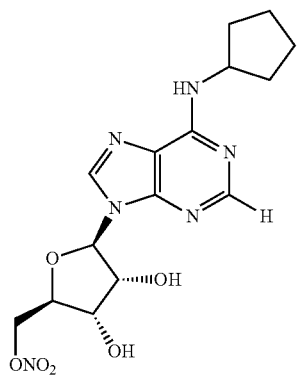

Compound A

18 Claims, 7 Drawing Sheets

(56) References Cited

U.S. PATENT DOCUMENTS

| | | |
|---|---|---|
| 5,801,159 A | 9/1998 | Miller et al. |
| 6,180,615 B1 | 1/2001 | Zablocki et al. |
| 6,214,807 B1 | 4/2001 | Zablocki et al. |
| 6,326,359 B1 | 12/2001 | Monaghan et al. |
| 6,358,536 B1 | 3/2002 | Thomas |
| 6,368,573 B1 | 4/2002 | Leung |
| 6,403,567 B1 | 6/2002 | Zablocki et al. |
| 6,403,649 B1 | 6/2002 | Woodward et al. |
| 6,407,076 B1 | 6/2002 | Box et al. |
| 6,426,337 B1 | 7/2002 | Cox et al. |
| 6,429,229 B1 | 8/2002 | Bouyssou et al. |
| 6,440,948 B1 | 8/2002 | Zablocki et al. |
| 6,448,236 B1 | 9/2002 | Monaghan et al. |
| 6,525,032 B2 | 2/2003 | Mantell et al. |
| 6,528,494 B2 | 3/2003 | Cox et al. |
| 6,528,516 B1 | 3/2003 | Civan et al. |
| 6,531,457 B2 | 3/2003 | Linden et al. |
| 6,534,486 B1 | 3/2003 | Allen et al. |
| 6,544,960 B1 | 4/2003 | Eldred et al. |
| 6,638,914 B1 | 10/2003 | Fishman et al. |
| 6,753,322 B2 | 6/2004 | Mantell et al. |
| 6,903,079 B2 | 6/2005 | Jagtap et al. |
| 6,921,753 B2 | 7/2005 | Mantell et al. |
| 7,084,127 B2 | 8/2006 | Van Tilburg et al. |
| 7,163,959 B2 | 1/2007 | Stjernschantz et al. |
| 7,189,706 B2 | 3/2007 | Van Tilburg et al. |
| 7,271,157 B2 | 9/2007 | Elzein et al. |
| 7,351,407 B2 | 4/2008 | Fleenor et al. |
| 7,423,144 B2 | 9/2008 | Jagtap et al. |
| 7,713,946 B2 | 5/2010 | Dhalla et al. |
| 7,732,424 B2 | 6/2010 | Jagtap et al. |
| 7,964,191 B2 | 6/2011 | Rodrigues et al. |
| 8,163,737 B2 | 4/2012 | Anderson et al. |
| 8,183,224 B2 | 5/2012 | Jagtap et al. |
| 8,207,215 B2 | 6/2012 | Muller et al. |
| 8,440,639 B2 | 5/2013 | Kim et al. |
| 8,455,457 B2 | 6/2013 | Kim et al. |
| 8,470,800 B2 | 6/2013 | Barman et al. |
| 8,476,247 B2 | 7/2013 | Kim et al. |
| 8,501,708 B2 | 8/2013 | Jagtap |
| 8,609,833 B2 | 12/2013 | Jagtap et al. |
| 8,648,169 B2 | 2/2014 | Saragovi |
| 8,784,886 B2 | 7/2014 | Fawzy et al. |
| 8,877,732 B2 | 11/2014 | Kim et al. |
| 8,895,530 B2 | 11/2014 | Kim et al. |
| 9,278,991 B2 | 3/2016 | McVicar |
| 9,289,383 B2 | 3/2016 | Kim et al. |
| 2001/0051612 A1 | 12/2001 | Cristalli |
| 2003/0013675 A1 | 1/2003 | Yeadon et al. |
| 2003/0055021 A1 | 3/2003 | DeNinno et al. |
| 2004/0166168 A1 | 8/2004 | Mathiowitz et al. |
| 2005/0250813 A1 | 11/2005 | Wieckhusen et al. |
| 2006/0009417 A1 | 1/2006 | Elzein et al. |
| 2006/0034941 A1 | 2/2006 | Dobson |
| 2007/0185051 A1 | 8/2007 | Dhalla et al. |
| 2007/0238694 A1 | 10/2007 | Salzman et al. |
| 2008/0050335 A1 | 2/2008 | Faour et al. |
| 2009/0131342 A1 | 5/2009 | Ellis |
| 2009/0220516 A1 | 9/2009 | Laties et al. |
| 2009/0258836 A1 | 10/2009 | Civan et al. |
| 2010/0041552 A1 | 2/2010 | Saxell et al. |
| 2010/0279970 A1 | 11/2010 | Barman et al. |
| 2010/0297121 A1 | 11/2010 | Mi |
| 2011/0123622 A1 | 5/2011 | Avery et al. |
| 2011/0172177 A1 | 7/2011 | Kim et al. |
| 2011/0217262 A1 | 9/2011 | Kornfield et al. |
| 2011/0245193 A1 | 10/2011 | Kim et al. |
| 2011/0245194 A1 | 10/2011 | Jagtap |
| 2011/0251151 A1 | 10/2011 | Kim et al. |
| 2012/0108672 A1 | 5/2012 | Tsutsui et al. |
| 2013/0196940 A1 | 8/2013 | McVicar |
| 2014/0018314 A1 | 1/2014 | Kim et al. |
| 2014/0271876 A1 | 9/2014 | McVicar et al. |
| 2014/0275128 A1 | 9/2014 | McVicar |
| 2015/0038448 A1 | 2/2015 | Kim et al. |
| 2015/0080330 A1 | 3/2015 | Kim et al. |

FOREIGN PATENT DOCUMENTS

| | | |
|---|---|---|
| CN | 101321460 A | 12/2008 |
| DE | 2342479 A1 | 3/1975 |
| EP | 0364417 A1 | 4/1990 |
| FR | 2186470 | 1/1974 |
| GB | 2436255 A | 9/2007 |
| JP | 2012-508764 A | 4/2012 |
| KR | 20030005241 A | 1/2003 |
| WO | 9300329 A1 | 1/1993 |
| WO | 93/23418 A1 | 11/1993 |
| WO | 94/02497 A1 | 2/1994 |
| WO | 95/02604 A1 | 1/1995 |
| WO | 95/11681 A1 | 5/1995 |
| WO | 96/02553 A2 | 2/1996 |
| WO | 97/33590 A1 | 9/1997 |
| WO | 97/33879 A1 | 9/1997 |
| WO | 98/08855 A2 | 3/1998 |
| WO | 98/50047 A1 | 11/1998 |
| WO | 99/20284 A1 | 4/1999 |
| WO | 01/19360 A2 | 3/2001 |
| WO | 01/40245 A1 | 6/2001 |
| WO | 01/45715 A2 | 6/2001 |
| WO | 02/9702 A2 | 2/2002 |
| WO | 02/055085 A2 | 7/2002 |
| WO | 02/083152 A1 | 10/2002 |
| WO | 03/029264 A2 | 4/2003 |
| WO | 03/088978 A1 | 10/2003 |
| WO | 2005117910 A2 | 12/2005 |
| WO | 2007/064795 A2 | 6/2007 |
| WO | 2008/130520 A1 | 10/2008 |
| WO | 2009076580 A2 | 6/2009 |
| WO | 2009100326 A1 | 8/2009 |
| WO | 2010/127210 A1 | 11/2010 |
| WO | 2011/077435 A1 | 6/2011 |
| WO | 2012/028585 A1 | 3/2012 |
| WO | 2013/049725 A2 | 4/2013 |

OTHER PUBLICATIONS

Frishman, William H. et al., "Topical Ophthalmic Beta-Adrenergic Blockade for the Treatment of Glaucoma and Ocular Hypertension," J. Clin. Pharmacol., vol. 34:795-803 (1994).

Gandolfi, Stefano et al., "Three-Month Comparison of Bimatoprost and Latanoprost in Patients With Glaucoma and Ocular Hypertension," Advances in Therapy, vol. 18(3):110-121 (2001).

Ghiardi, G. et al., "The Purine Nucleoside Adenosine in Retinal Ischemia-Reperfusion Injury," Vision Research, vol. 39:2519-2535 (1999).

Gurwood, Andrew S., "Comparing selective laser trabeculoplasty witih Latanoprost for the control of intraocular pressure," Br J. Ophthalmol. vol. 89(11)1413-1417 (2005).

Hasko, Gyorgy et al., "Adenosine Receptor Agonists Differentially Regulate IL-10, TNF-a, and Nitric Oxide Production in RAW 264.7 Macrophages and in Endotoxemic Mice," The Journal of Immunology, vol. 157:4634-4640 (1996).

Hirao, Mami et al., "Effects of adenosine on optic nerve head circulation in rabbits," Experimental Eye Research, vol. 79:729-735 (2004).

Homma, Hiroshi et al., "Nucleosides and Nucleotides. 112. 2-(1Hexyn-1-yl)adenosine-5'-uronamides: A New Entry of Selective A2 Adenosine Receptor Agonists with Potent Antihypertensive Activity," J. Med. Chem., vol. 35:2881-2890 (1992). cited byapplicant.

Houlsby, R.D., et al., "Antimicrobial activity of borate-buffered solutions," Antimicrob Agents Chemother., vol. 29(5): 803-806 (1986).

Husain, S. et al., "Mechanisms Linking Adenosine A1 Receptors and Extracellular Signal-Regulated Kinase 1/2 Activation in Human Trabecular Meshwork Cells," The Journal of Pharmacology and Experimental Therapeutics, vol. 320(1)258-265 (2006).

(56) References Cited

OTHER PUBLICATIONS

Hutchison, Alan J. et al., "2-(Arylalkylamino)adenosin-5'-uronamides: A New Class of Highly Selective Adenosine A2 Receptor Ligands," J. Med. Chem., vol. 33:1919-1924 (1990).
International Search Report and Written Opinion for Application No. PCT/US2013/023166, 15 pages, dated Apr. 17, 2013.
Jacobson, Kenneth A. et al., "Adenosine receptors as therapeutic targets," Nature Reviews Drug Discovery, vol. 5:247-264 (2006).
Jagtap, Prakash G. et al., "2-(N-Acyl) and 2-N-acyl-N6-substituted analogues of adenosine and their affinity at the human adenosine receptors," Bioorganic & Medicinal Chemistry Letters, vol. 14:1495-1498 (2004).
Karl, Mike O. et al., "Differential P1-purinergic modulation of human Schlemm's canal inner-wall cells," Am. J. Physiol. well Physiol., vol. 288:C784-C794 (2005).
Kim, N. et al., "INO-8875, An Adenosine A1 Agonist, in Development for Open-Angle Glaucoma Reduces IOP in Three Rabbit Models," Investigative Ophthalmology & Visual Science, vol. 50, E-Abstract 4061 (2009).
Klotz, K. N. et al., "Comparative pharmacology of human adenosine receptor subtypes—characterization of stably transfected receptors in CHO cells," Naunyn-Schmiedeberg's Arch. Pharmacol., vol. 357:1-9 (1997).
Klotz, Karl-Norbert et al., "Photoaffinity Labeling of A1-adenosine Receptors," The Journal of Biological Chemistry, vol. 260(27):14659-14664 (1985).
Knutsen, Lars J.S. et al., "N-Substituted Adenosines as Novel Neuroprotective A1 Agonists with Dimished Hypotensive Effects," J. Med. Chem., vol. 42:3463-3477 (1999).
Konno, Takashi et al., "2-(1-Hexyn-1-yl)adenosine-induced intraocular hypertension is mediated via K+ channel opening through adenosine A2A receptor in rabbits," European Journal of Pharmacology, vol. 518:203-211 (2005).
Konno, Takashi et al., "Effect of chymase on intraocular pressure in rabbits," European Journal of Pharmacology, vol. 524:132-137 (2005).
Konno, Takashi et al., "Involvement of Adenosine A2a Receptor in Intraocular Pressure Decrease Induced by 2-(1-Octyn-1-yl)adenosine or 2-(6-Cyano-I-hexyn-1-yl)adenosine," J. Pharmacol. Sci., vol. 97:501-509 (2005).
Kristinsson et al., Herbicidally Active Sulfamoyl Nucleosides: Isolation and Synthesis Synthesis and Chemistry anf Agrochemicals IV, published 1995 by American Chemical Society, chapter 19, pp. 206-219.
Kunkel, Steven L. et al., "The role of chemokines in inflammatory joint disease," Journal of Leukocyte Biology, vol. 59:6-12 (1996).
Lesar, Timothy S., "Comparison of ophthalmic beta-blocking agents," Clinical Pharmacy, vol. 6:451-463 (1987).
Lichtenthaler, F.W. et al., "Nucleosides, XVIII1. Improved Preparation of Nucleoside 5'-Nitrates," Synthesis, vol. 27:199-201 (1973).
Lohse, Martin J. et al., "8-Cyclopentyl-1,3-dipropylxanthine (DPCPX)—a selective high affinity antagonist radioligand for A1 adenosine receptors," Naunyn-Schmiedeberg's Arch. Pharmacol., vol. 336:204-210 (1987).
Mager, P.P. et al., "Molecular simulation applied to 2-(N'-alkylidenehydrazino)- and 2-(N'-aralkylidenehydrazino) adenosine A2 agonists," Eur. J. Med. Chem., vol. 30:15-25 (1995).
Maillard, Michel C. et al., "Adenosine Receptor Prodrugs: Synthesis and Biological Activity of Derivatives of Potent, A1-Selective Agonists," Journal of Pharmaceutical Sciences, vol. 83(1):46-53 (1994).
Matsuda, Akira et al., "Nucleosides and Nucleotides. 103. 2-Alkynyladenosines: A Novel Class of Selective Adenosine A2 Receptor Agonists with Potent Antihypertensive Effects," J. Med. Chem., vol. 35:241-252 (1992).
McKenzie, Sheila G. et al., "Effects of Adenosine and Related Compounds on Adenylate Cyclase and Cyclic AMP Levels in Smooth Muscle," European Journal of Pharmacology, vol. 41:193-203 (1977).

McWhinney, Charlene D. et al., "Activation of adenosine A3 receptors on macrophages inhibits tumor necrosis factor-a," European Journal of Pharmacology, vol. 310:209-216 (1996).
Mincione, Francesco et al., "The Development of Topically Acting Carbonic Anhydrase Inhibitors as Antiglaucoma Agents," Current Pharmaceutical Design, vol. 14:649-654 (2008).
Missiaen, Ludwig et al., "Effect of adenine nucleosides on myoinositol-1,4,5-trisphosphate-induced calcium release," Biochem. J., vol. 325:661-666 (1997).
Mitchell, C. et al., "The P2X7 Receptor in Retinal Ganglion Cells: A neuronal model of pressure-induced damage and protection by a shifting purinergic balance," Purinergic Signalling, vol. 4, pp. 313-321 (2008).
Moos, Walter H. et al., "N6-Cycloalkyladenosines. Potent A1-Selective Adenosine Agonists," Journal of Medicinal Chemistry, vol. 28(10):1383-1384 (1985).
Muller, C.E. et al., "Adenosine Receptor Ligands-Recent Developments Part I. Agonists," Current Medicinal Chemistry, vol. 7:1269-1288 (2000).
Nair, Vasu et al., "Novel, Stable Congeners of the Antiretroviral Compound 2',3'-Dideoxyadenosine," J. Am. Chem. Soc., vol. 111:8502-8504 (1989).
Nell, Peter G. et al., "The Adenosine A1 Receptor and its Ligands," Progress in Medicinal Chemistry, vol. 47:163-201 (2009).
Niiya, Kazunori et al., "2-(N'-Alkylidenehydrazino)adenosines: Potent and Selective Coronary Vasodilators," J. Med. Chem., vol. 35:4557-4561 (1992).
O'Neil et al. (eds.), "The Merck Index, 14th Edition," Merck & Co., Whitehouse Station, NJ, pp. 1693 (2006).
Ohno, Michihiro et al., "Modulation of adenosine receptor affinity and intrinsic efficacy in adenine nucleosides substituted at the 2-position," Bioorganic & Medicinal Chemistry, vol. 12:2995-3007 (2004).
Dngini, Ennio et al., "Pharmacology of adenosine A2A receptors," TiPS, vol. 17:364-372 (1996).
Drzalesi, N. et al., "Comparison of the Effects of Latanoprost, Travoprost, and Bimatoprost on Circadian Intraocular Pressure in Patients with Glaucoma or Ocular Hypertension," Ophthalmology, vol. 113:239-246 (2006).
Parmely, Michael J. et al., "Adenosine and a Related Carbocyclic Nucleoside Analogue Selectively Inhibit Tumor Necrosis Factor-a Production and Protect Mice against Endotoxin Challenge," The Journal of Immunology, vol. 151 (1):389-396 (1993).
Pitcher, Graham M. et al., "Paw withdrawal threshold in the von Frey hair test is influenced by the surface on which the rat stands," Journal of Neuroscience Methods, vol. 87:185-193 (1999).
Polska, Elzbieta et al., "Effects of Adenosine on Intraocular Pressure, Optic Nerve Head Blood Flow, and Choroidal Blood Flow in Healthy Humans," Investigative Ophthalmology & Visual Science, vol. 44(7):3110-3114 (2003).
Ralevic, Vera et al., "Receptors for Purines and Pyrimidines," Pharmacological Reviews, vol. 50(3):413-492 (1998).
Reinhart, Konrad et al., "Assessment of the safety and efficacy of the monoclonal anti-tumor necrosis factor antibody-fragment, MAK 195F, in patients with sepsis and septic shock: A multicenter, randomized, placebo-controlled, dose-ranging study,"Crit. Care Med., vol. 24(5):733-742 (1996).
Reinstein, Leon J. et al., "Suppression of Lipopolysaccharide-stimulated Release of Tumor Necrosis Factor by Adenosine: Evidence for A2 Receptors on Rat Kupffer Cells," Hepatology, vol. 19:1445-1452 (1994).
Riche, Florence et al., "High tumor necrosis factor serum level is associated with increased survival in patients with abdominal septic shock: A prospective study in 59 patients," Surgery, vol. 120(5):801-807 (1996).
Rieger, Jayson M. et al., "Design, Synthesis, and Evaluation of Novel A2A Adenosine Receptor Agonists," J. Med. Chem., vol. 44:531-539 (2001).
Robinson, Ralph P. et al., "Discovery of the Humifumarate and (alpha-L-Alanyloxy)methyl Ether as Prodrugs of an Antirheumatic Oxindole: Prodrugs for the Enolic OH Group," J. Med. Chem., vol. 39:10-18 (1996).

(56) References Cited

OTHER PUBLICATIONS

Roelen, Harlof et al., "N6,C8-Disubstituted Adenosine Derivatives as Partial Agonists for Adenosine A1 Receptors," J. Med. Chem., vol. 39:1463-1471 (1996).
Sajjadi, Fereydoun G. et al., "Inhibition of TNF-a Expression by Adenosine," The Journal of Immunology, vol. 156:3435-3442 (1996).
Schleef, Raymond R. et al., "The Effect of Fibrin on Endothelial Cell Migration in Vitro," Tissue & Cell, vol. 14 (4):629-636 (1982).
Shuman, Dennis A. et al., "The Synthesis of Nucleoside Sulfamates Related to Nucleocidin," Journal of the American chemical Society, vol. 92(11):3434-3440 (1970).
Soulere, Laurent et al., "Synthesis and Uptake of Nitric Oxide-Releasing Drugs by the P2 Nucleoside Transporter in *Trypanosoma equiperdum*," Bioorganic & Medicinal Chemistry Letters, vol. 10:1347-1350 (2000).
Stewart, W., "Perspectives in the medical treatment of glaucoma," Current Opinion in Ophthalmology, vol. 10:99-108 (1999).
Stewart, William C. et al., "Beta-Blocker-Induced Complications and the Patient With Glaucoma," Archives of Internal Medicine, vol. 158(3):221-226 (1998).
Sugrue, Michael F., "Pharmacological and Ocular Hypotensive Properties of Topical Carbonic Anhydrase Inhibitors," Progress in Retinal and Eye Research, vol. 19(1):87-112 (2000).
Supplementary European Search Report for Application No. 05757108, dated Jun. 4, 2007.
Supplementary European Search Report for Application No. 11732309.7, 9 pages, dated Jul. 31, 2013.
Supplementary European Search Report for Application No. 11760282.1, 7 pages, dated Jul. 19, 2013.
Thompson, Robert D. et al., "Activity of N6-Substituted 2-Chloroadenosines at A1 and A2 Adenosine Receptors," J. Med. Chem., vol. 34:3388-3390 (1991).
Tian, Baohe et al., "Effects of Adenosine Agonists on Intraocular Pressure and Aqueous Humor Dynamics in Cynomolgus Monkeys," Exp. Eye Res., vol. 64:979-989 (1997).
Tsilimbaris, Miltiadis K. et al., "The Use of Atomic Force Microscopy for the Observation of Corneal Epithelium Surface," Invest. Ophthalmol. Vis. Sci., vol. 41:680-686 (2000).
U.S. Appl. No. 12/771,289, First Office Action on the Merits (FAOM), mailed May 23, 2012.
U.S. Appl. No. 13/051,633, First Office Action on the Merits (FAOM), mailed May 17, 2012, 32 pages.
U.S. Appl. No. 13/051,655, First Office Action on the Merits (FAOM), mailed May 16, 2012, 28 pages.
U.S. Appl. No. 13/051,655, First Office Action on the Merits (FAOM), mailed May 16, 2012.
U.S. Appl. No. 13/072,349, First Office Action on the Merits (FAOM), mailed Mar. 27, 2012, 164 pages.
U.S. Appl. No. 13/072,349, First Office Action on the Merits (FAOM), mailed Mar. 27, 2012.
Van Der Wenden, Eleonora M. et al., "5'Substituted Adenosine Analogs as New High-Affinity Partial Agonists for the Adenosine A1 Receptor," J. Med. Chem., vol. 41:102-108 (1998).
Van Tilburg, Erica W. et al., "2,5'-Disubstituted Adenosine Derivatives: Evaluation of Selectivity and Efficacy for the Adenosine A1, A2A and A3 Receptor," J. Med. Chem., vol. 45:420-429 (2002).
Virag, Laszlo et al., "Effects of poly(ADP-ribose) polymerase inhibition on inflammatory cell migration in a murine model of asthma," Med. Sci. Monit., vol. 10(3):BR77-83 (2004).
Vittori, Sauro et al., "2-Alkenyl and 2-Alkyl Derivatives of Adenosine and Adenosine-5'-N-Ethyluronamide: Different Affinity and Selectivity of E- and Z-Diastereomers at A2A Adenosine Receptors," J. Med. Chem., vol. 39:4211-4217 (1996). cited byapplicant.
Vittori, Sauro et al., "N-Cycloalkyl Derivatives of Adenosine and 1-Deazaadenosine as Agonists and Partial Agonists of the A1 Adenosine Receptor," J. Med. Chem., vol. 43:250-260 (2000).

Viziano, Monica et al., "2-[N'-(3-Arylallylidene)hydrazino]adenosines Showing A2a Adenosine Agonist Properties and Vasodilation Activity," J. Med. Chem., vol. 38:3581-3585 (1995).
Witte, M.B. et al., "Nitric oxide enhances experimental wound healing in diabetes," British Journal of Surgery, vol. 89:1594-1601 (2002).
Woodward, D. et al., "Fixed-Combination and Emerging Glaucoma Therapies," Expert Opinion on Emerging Drugs, 2007, vol. 12(2):313-327 (2007).
Accession No. 1994:153455, Higuchi, T. et al., "Evaluation of Serum Lactate-Dehydrogenase Activity for Estimation of Energy-Expenditure in Human-Subjects," Ergonomics, vol. 37(3):389-397 (1994).
Accession No. 2001:494425, Martin, H. et al., "The Guardian/Observer: Information developments since 1998," Aslib Proceedings, vol. 53(5):161-166 (2001).
Accession No. 2002:660483, Shore, G.M. et al., "eta (eta)->gamma gamma: A tale of two anomalies," Physica Scripta, vol. T99:84-95 (2002).
Accession No. 2004:827690, Tacke, R. et al., "Sila-haloperidol: a silicon analogue of the dopamine (D-2) receptor antagonist haloperidol," Organometallics, vol. 23(19):4468-4477 (2004).
ACS Registry No. 151563-23-4 (1993).
ACS Registry No. 365533-72-8 (2001).
ACS Registry No. 365533-73-9 (2001).
ACS Registry No. 365533-74-0 (2001).
Al-Mughales, J. et al., "The chemoattractant activity of rheumatoid synovial fluid for human lymphocytes is due to multiple cytokines," Clin. Exp. Immunol., vol. 106:230-236 (1996).
Appel, S. et al., "Modelling of the pharmacodynamic interaction of an A1 adenosine receptor agonist and antagonist in vivo: N6-cyclopentyladenosine and 8-cyclopentyltheophylline," British Journal of Pharmacology, vol. 115:1253-1259 (1995). cited byapplicant.
Avila, Marcel Y. et al., "A1-,A2A-and A3-subtype adenosine receptors modulate intraocular pressure in the mouse," British Journal of Pharmacology, vol. 134:241-245 (2001).
Baraldi, Pier Giovanni et al., "Synthesis and Biological Activity of a New Series of N6-Arylcarbamoyl, 2-(Ar)alkynyl-N6-arylcarbamoyl, and N6-Carboxamido Derivatives of Adenosine-5'-N-ethyluronamide as A1 and A3 Adenosine Receptor Agonists," J. Med.Chem., vol. 41:3174-3185 (1998).
Bell, Jerald, A. et al., "Ocular Hypertension," eMedicine Ophthalmology, retreived online at: http://emedicine.medscape.com/article/1207470-overview (2008).
Beukers, Margot W. et al., "N6-Cyclopentyl-2-(3-phenylaminocarbonyltriazene-1-yl)adenosine (TCPA), a Very Selective Agonist with High Affinity for the Human Adenosine A1 Receptor," J. Med. Chem., vol. 46:1492-1503 (2003).
Beukers, Margot W. et al., "New, Non-Adenosine, High-Potency Agonists for the Human Adenosine A2B Receptor with an Improved Selectivity Profile Compared to the Reference Agonists N-Ethylcarboxamidoadenosine," Journal of Medicinal Chemistry, vol. 47(15):3707-3709 (2004).
Bouma, Maarten G. et al., "Differential Regulatory Effects of Adenosine on Cytokine Release by Activated Human Monocytes," The Journal of Immunology, vol. 153:4159-4168 (1994).
Bradley, Karri K. et al., "Purine Nucleoside-Dependent Inhibition of Cellular Proliferation in 1321N1 Human Astrocytoma Cells," The Journal of Pharmacology and Experimental Therapeutics, vol. 299(2):748-752 (2001).
Broadley, Kenneth J. et al., "Drugs modulating adenosine receptors as potential therapeutic agents for cardiovascular diseases," Exp. Opin. Ther. Patents, vol. 10(11):1669-1692 (2000).
Brooks, Anne M.V. et al., "Ocular beta-Blockers in Glaucoma Management, Clinical Pharmacological Aspects," Drugs & Aging, vol. 2(3):208-221 (1992).
BROWN, M. R. W., et al., "The preservation of ophthalmic preparations," J. Soc. Cosmetic Chemists, vol. 16, pp. 369-393 (1965).
Bruns, R. et al., "Adenosine receptor activation in human fibroblasts: nucleoside agonists and antagonists," Can. J. Physiol. Pharmacol., vol. 58:673-691 (1979).

(56) References Cited

OTHER PUBLICATIONS

Bruns, Robert F. et al., "Characterization of the A2 Adenosine Receptor Labeled by [3H]NECA in Rat Striatal Membrans," Biological Pharmacology, vol. 89:331-346 (1986).
Bruns, Robert F., "Adenosine receptor activation in human fibroblasts: nucleoside agonists and antagonists," Can. J. Physiol. Pharmacol., vol. 58:673-691 (1979).
Camaioni, Emidio et al., "Adenosine Receptor Agonists: Synthesis and Biological Evaluation of the Diastereoisomers of 2-(3-Hydroxy-3-phenyl-1-propyn-1-yl)NECA," Bioorganic & Medicinal Chemistry, vol. 5(12):2267-2275 (1997).
Chinese Office Action for Application No. 201080018539.X, 9 pages, dated Nov. 2, 2012.
Costenla, A. et al., "An Adenosine Analogue Inhibits Nmda Receptor-Mediated Responses in Bipolar Cells of Rat Retina," Exp. Eye Res., vol. 68: 367-370 (1999).
Cristalli, Gloria et al., "2-Alkynyl Derivatives of Adenosine and Adenosine-5'N-ethyluronamide as Selective Agonists at A2 Adenosine Receptors," J. Med. Chem., vol. 35:2363-2368 (1991).
Cristalli, Gloria et al., "2-Alkynyl Derivatives of Adenosine-5'-N-ethyluronamide: Selective A2 Adenosine Receptor Agonists with Potent Inhibitory Activity on Platelet Aggregation," J. Med. Chem., vol. 37:1720-1726 (1994).
Cristalli, Gloria et al., "2-Aralkynyl and 2-Heteroalkynyl Derivatives of Adenosine-5'-N-ethyluronamide as Selective A2a Adenosine Receptor Agonists," J. Med. Chem., vol. 38:1462-1472 (1995).
Crosson, Craig E. et al., "Characterization of Ocular Hypertension Induced by Adenosine Agonists," Investigative Ophthalmology & Visual Science, vol. 37(9):1833-1839 (1996).
Crosson, Craig E. et al., "Intraocular Pressure Responses to the Adenosine Agonist Cyclohexyladenosine: Evidence for a Dual Mechanism of Action," Investigative Ophthalmology & Visual Science, vol. 42(8):1837-1840 (2001).
Crosson, Craig E. et al., "Modulation of Conventional Outflow Facility by the Adenosine AI Agonist N6-Cyclohexyladenosine," Investigative Ophthalmology & Visual Science, vol. 46(10):3795-3799 (2005).
Crosson, Craig E. et al., "Modulation of Intraocular Pressure by Adenosine Agonists," Journal of Ocular Pharmacology, vol. 10(1):379-383 (1994).
Crosson, Craig E. et al., "Ocular effects associated with the chronic administration of the adenosine A1 agonist cyclohexyladenosine," Current Eye Research, vol. 21(4):808-813 (2000).
Crosson, Craig E., "Adenosine Receptor Activation Modulates Intraocular Pressure in Rabbits," The Journal of Pharmacology and Experimental Therapeutics, vol. 273(1):320-326 (1995).
Crosson, Craig E., "Intraocular Pressure Responses to the Adenosine Agonist Cyclohexyladenosine: Evidence for a Dual Mechanism of Action," Investigative Ophthalmology & Visual Science, vol. 42(8):1837-1840 (2001).
Crosson, Craig E., "Ocular hypotensive activity of the adenosine agonist (R)-phenylisopropyladenosine in rabbits," Current Eye Research, vol. 11(5):453-458 (1992).
Daines, Bradley S. et al., "Intraocular Adenosine Levels in Normal and Ocular-Hypertensive Patients," Journal of Ocular Pharmacology and Therapeutics, vol. 19(2):113-119 (2003).
Dalpiaz, Alessandro et al., "Development and characterization of biodegradable nanospheres as delivery systems of anti-ischemic adenosine derivatives," Biomaterials, vol. 26:1299-1306 (2005).
Dalpiaz, Alessandro et al., "Fabrication Via a Nonaqueous Nanoprecipitation Method, Characterization and In Vitro Biological Behavior of N6-Cyclopentyladenosine-Loaded Nanoparticles," Journal of Pharmaceutical Sciences, vol. 98 (11):4272-4284(2009).
Dalpiaz, Alessandro et al., "Synthesis and Study of 5'-Ester Prodrugs of N6-Cyclopentyladenosine, a Selective A1 Receptor Agonist," Pharmaceutical Research, vol. 18(4):531-536 (2001).
De Lean, Andre et al., "Validation and Statistical Analysis of a Computer Modeling Method for Quantitative Analysis of Radioligand Binding Data for Mixtures of Pharmacological Receptor Subtypes," Molecular Pharmacology, vol. 21:5-16 (1982). cited byapplicant.
Deninno, Michael P. et al., "3'-Aminoadenosine-5'-uronamides: Discovery of the First Highly Selective Agonist at the Human Adenosine A3 Receptor," J. Med. Chem., vol. 46:353-355 (2003).
Elzein, Elfatih et al., "A1 adenosine receptor agonists and their potential therapeutic applications," Expert Opinion on Investigational Drugs, vol. 17(12):1901-1910 (2008).
Epple et al., "Solid-Phase Synthesis of Nucleoside Analogues" Journal of Combinatorial Chemistry (2003) vol. 5 pp. 292-310.
Fisher, Charles J. Jr. et al., "Treatment of Septic Shock with the Tumor Necrosis Factor Receptor : Fc Fusion Protein," N. Engl. J. Med., vol. 334(26)1697-1702 (1996).
Fleischhauer, J.C. et al., "Common Actions of Adenosine Receptor Agonists in Modulating Human Trabecular Meshwork Cell Transport," J. Membrane Biol., vol. 193:121-136 (2003).
Fleisher, David et al., "Improved oral drug delivery: solubility limitations overcome by the use of prodrugs," Advanced Drug Delivery Reviews, vol. 19:115-130 (1996).
Follmann, Hartmut et al., "Adenine Nucleosides in Solution: Circular Dichroism Studies and Base Conformation," Eur. J. Biochem., vol. 58:31-41 (1975).
Francis, John E. et al., "Highly Selective Adenosine A2 Receptor Agonists in a Series of N-Alkylated 2-Aminoadenosines," J. Med. Chem., vol. 34:2570-2579 (1991).
U.S. Appl. No. 11/137,632, filed May 25, 2005, P. Jagtap.
U.S. Appl. No. 12/221,539, filed Aug. 4, 2008, P. Jagtap.
U.S. Appl. No. 13/451,613, filed Apr. 20, 2012, P. Jagtap.
U.S. Appl. No. 12/771,289, filed Apr. 30, 2010, P. Jagtap.
U.S. Appl. No. 13/855,919, filed Apr. 3, 2013, Shikha Barman.
U.S. Appl. No. 13/004,380, filed Jan. 11, 2011, N. N. Kim.
U.S. Appl. No. 14/517,509, filed Oct. 17, 2014, N. N. Kim.
U.S. Appl. No. 13/051,633, filed Mar. 18, 2011, N. N. Kim.
U.S. Appl. No. 13/051,655, filed Mar. 18, 2011, N. N. Kim.
U.S. Appl. No. 13/071,993, filed Mar. 25, 2011, P. Jagtap.
U.S. Appl. No. 13/072,349, filed Mar. 25, 2011, N. N. Kim.
U.S. Appl. No. 13/909,288, filed Jun. 4, 2013, N. N. Kim.
U.S. Appl. No. 14/552,160, filed Nov. 2, 2014, N. N. Kim.
U.S. Appl. No. 15/044,705, filed Feb. 16, 2016, N. N. Kim.
U.S. Appl. No. 13/750,389, filed Jan. 25, 2013, W. McVicar.
U.S. Appl. No. 14/211,516, filed Mar. 14, 2014, W. McVicar.
U.S. Appl. No. 14/211,567, filed Mar. 14, 2014, W. McVicar.
U.S. Appl. No. 14/957,170, filed Dec. 2, 2015, W. McVicar.
U.S. Appl. No. 11/137,632, filed Jun. 23, 2008, Eric Olson.
U.S. Appl. No. 11/137,632, filed Nov. 8, 2007, Eric Olson.
U.S. Appl. No. 11/137,632, filed May 9, 2007, Eric Olson.
U.S. Appl. No. 12/221,539, filed Jan. 23, 2012, Eric Olson.
U.S. Appl. No. 12/221,539, filed Sep. 2, 2011, Eric Olson.
U.S. Appl. No. 12/221,539, filed Apr. 28, 2011, Eric Olson.
U.S. Appl. No. 12/221,539, filed Sep. 22, 2010, Eric Olson.
U.S. Appl. No. 13/451,613, filed Aug. 15, 2013, Eric Olson.
U.S. Appl. No. 13/451,613, filed Dec. 17, 2012, Eric Olson.
U.S. Appl. No. 12/771,289, filed May 16, 2013, Lawrence E. Crane.
U.S. Appl. No. 12/771,289, filed Jan. 3, 2013, Lawrence E. Crane.
U.S. Appl. No. 12/771,289, filed May 23, 2012, Lawrence E. Crane.
U.S. Appl. No. 13/855,919, filed Aug. 14, 2013, Lawrence E. Crane.
U.S. Appl. No. 13/004,380, filed Jun. 24, 2014, Lawrence E. Crane.
U.S. Appl. No. 13/004,380, filed Sep. 10, 2013, Lawrence E. Crane.
U.S. Appl. No. 13/004,380, filed Mar. 14, 2013, Lawrence E. Crane.
U.S. Appl. No. 13/004,380, filed Sep. 10, 2012, Michael Henry.
U.S. Appl. No. 14/517,509, filed Feb. 18, 2016, Lawrence E. Crane.
U.S. Appl. No. 14/517,509, filed Sep. 11, 2015, Lawrence E. Crane.
U.S. Appl. No. 14/517,509, filed Feb. 26, 2015, Lawrence E. Crane.
U.S. Appl. No. 13/051,633, filed Jan. 14, 2013, Lawrence E. Crane.
U.S. Appl. No. 13/051,633, filed May 17, 2012, Lawrence E. Crane.
U.S. Appl. No. 13/051,655, filed Feb. 4, 2013, Lawrence E. Crane.
U.S. Appl. No. 13/051,655, filed May 16, 2012, Lawrence E. Crane.
U.S. Appl. No. 13/071,993, filed Apr. 3, 2013, Lawrence E. Crane.
U.S. Appl. No. 13/071,993, filed Jan. 8, 2013, Lawrence E. Crane.
U.S. Appl. No. 13/071,993, filed Jun. 13, 2012, Lawrence E. Crane.
U.S. Appl. No. 13/072,349, filed Mar. 4, 2013, Lawrence E. Crane.
U.S. Appl. No. 13/072,349, filed Mar. 27, 2012, Lawrence E. Crane.

(56) References Cited

OTHER PUBLICATIONS

U.S. Appl. No. 13/750,389, filed Sep. 23, 2014, Lawrence E. Crane.
U.S. Appl. No. 13/909,288, filed Jul. 24, 2014, Lawrence E. Crane.
U.S. Appl. No. 13/909,288, filed Jan. 2, 2014, Lawrence E. Crane.
U.S. Appl. No. 13/750,389, filed Dec. 3, 2015, Lawrence E. Crane.
U.S. Appl. No. 13/750,389, filed Oct. 26, 2015, Lawrence E. Crane.
U.S. Appl. No. 13/750,389, filed May 21, 2015, Lawrence E. Crane.
U.S. Appl. No. 14/211,516, filed Jan. 8, 2016, T. Nielsen.
U.S. Appl. No. 14/211,516, filed Aug. 26, 2015, T. Nielsen.
U.S. Appl. No. 14/211,567, filed Oct. 26, 2015, S. Moore.
U.S. Appl. No. 14/211,567, filed May 13, 2015, S. Moore.
U.S. Appl. No. 14/211,567, filed Jun. 3, 2016, S. Moore.

ANHYDROUS POLYMORPHS OF [(2R,3S,4R,5R)-5-(6-(CYCLOPENTYLAMINO)-9H-PURIN-9-YL)-3,4-DIHYDROXYTETRA-HYDROFURAN-2-YL)] METHYL NITRATE AND PROCESSES OF PREPARATION THEREOF

CROSS-REFERENCE TO RELATED APPLICATIONS

This application is a continuation of U.S. application Ser. No. 13/750,389, filed on Jan. 25, 2013, which issued as U.S. Pat. No. 9,278,991 on Mar. 8, 2016, which claims priority to, and the benefit of, U.S. Provisional Application No. 61/591,037, filed on Jan. 26, 2012. The entire contents of the aforementioned application and any patents, patent applications, and references cited throughout this specification are herein incorporated by reference in their entireties.

FIELD OF THE INVENTION

The present invention provides novel anhydrous polymorph forms of [2R,3S,4R,5R)-5-(6-(cyclopentylamino)-9H-purin-9-yl)-3,4-dihydroxytetrahydrofuran-2-yl)]methyl nitrate (Compound A) and to processes of preparation thereof.

BACKGROUND OF THE INVENTION

Compound A is represented by the following structure

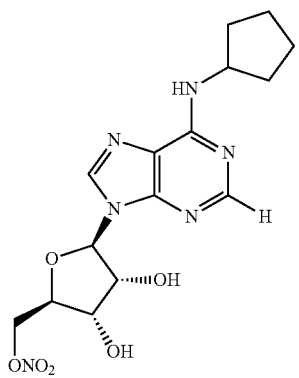

[(2R,3S,4R,5R)-5-(6-(cyclopentylamino)-9H-purin-9-yl)-3,4-dihydroxytetrahydrofuran-2-yl)]methyl nitrate, Compound A is a selective adenosine $A_1$ receptor agonist and is of particular use in the treatment of elevated intraocular pressure as described in PCT/US2010/033112 (published as WO2010/127210).

Compound A can be prepared using the procedures described in U.S. Pat. No. 7,423,144, US 20090062314, and WO2010/127210 all of which are herein incorporated by reference in their entirety.

Many pharmaceutical solids can exist in different physical forms. Polymorphism can be characterized as the ability of a drug substance to exist in two or more crystalline phases that have different arrangements and/or conformations of the molecules in the crystal lattice.

Polymorphs of a pharmaceutical solid can have different physical and solid state chemical properties. The most stable polymorphic form of a drug substance is often used because it has the lowest potential for conversion from one polymorphic form to another.

A particular crystalline form of a compound can have physical properties that differ from those of other polymorphic forms and such properties can influence the physicochemical and pharmaceutical processing of the compound, particularly when the compound is prepared or used on a commercial scale. Such differences may alter the mechanical handling properties of the compound, such as dispersion in a blend of solid formulation excipients or within a suspension formulation. Polymorphs are also known in some cases to have different chemical stability profiles and different solubility of the solid material. As a result of these potential polymorph-specific physiochemical differences, the discovery of new polymorphic forms provides a new opportunity to improve the manufacturing or characteristics of a pharmaceutical end product.

Further, new polymorphic forms of a drug substance can display different melting point, hygroscopicity, stability, solubility and/or dissolution rate, crystallinity, crystal properties, and formulation handling characteristics, which are among the numerous properties that need to be considered in preparing medicament that can be effectively administered, they can materially impact the quality of a pharmaceutical product. Furthermore, regulatory agencies require a definitive knowledge, characterization and control of the polymorphic form of the active component in pharmaceutical dosage forms if it is in the solid state.

Compound A is under development by the Applicants for reducing intraocular pressure. The Applicants have found a number of polymorphs of Compound A that are useful for controlling certain desirable formulation properties. In particular two anhydrous forms have been identified, isolated and characterized.

SUMMARY OF INVENTION

Provided herein are anhydrous polymorphs of Compound A, and methods of preparation thereof.

Thus, in a first aspect there is provided an isolated anhydrous polymorph A1 of Compound A having the following crystal data, $C_{15}H_{20}N_6O_6$;
Mr=380.37;
Monoclinic crystal system;
$P2_1$ space group;
a=5.546(2) Å;
b=7.107(2) Å;
c=21.929(9) Å;
V=858.8(5) Å$^3$, and
Z=2.

In another aspect there is provided an isolated polymorph A1 of Compound A having substantially equivalent peaks at a reflection angle 2-theta as shown in Table 3.

In one embodiment there is provided an isolated polymorph of form A1 as defined above that is at least about 75% free of other polymorphic forms.

In one embodiment there is provided an isolated polymorph as defined above that is at least about 80% free of other polymorphic forms.

In one embodiment there is provided an isolated polymorph as defined above that is at least about 90% free of other polymorphic forms.

In one embodiment there is provided an isolated polymorph as defined above that is at least about 95% free of other polymorphic forms.

In one embodiment there is provided an isolated polymorph as defined above that is at least about 99% free of other polymorphic forms.

In one embodiment there is provided an isolated polymorph as defined above that is 100% free of other forms.

In another aspect there is provided a method of obtaining the polymorph A1, the method comprising the steps of taking Compound A and recrystallizing from ethanol.

In another aspect there is provided a method of obtaining the polymorph A1, the method comprising the steps of taking Compound A and recrystallizing from isopropanol, ethyl acetate, or isopropyl acetate.

In another aspect there is provided a method of obtaining the polymorph A1, the method comprising the steps of taking Compound A and recrystallizing from 1,4 dioxane, 2-methoxy ethanol, 3-methyl-2-butanone, methylethyl ketone, or 1,2-dimethoxyethane.

In another aspect there is provided a pharmaceutical composition comprising polymorph A1 as defined above and further comprising one or more pharmaceutically acceptable ingredients selected from the group consisting of carriers, excipients, diluents, additives, fillers, surfactants, binders, antimicrobial preservatives, viscosity enhancing agents, and buffers.

In one embodiment the pharmaceutical composition comprising polymorph A1 defined above is formulated for ophthalmic administration.

In a further aspect, there is also provided a method of treating a subject in need of a selective adenosine $A_1$ agonist, the method comprising administering to a subject in need thereof a therapeutically effective amount of the polymorph A1 defined above.

In a further aspect, there is also provided a method of reducing intraocular pressure in a subject, the method comprising topically administering to an eye of a subject in need thereof a therapeutically effective amount of the polymorph A1 defined above.

Thus, in another aspect there is provided a polymorph A2 of Compound A having the following crystal data, $C_{15}H_{20}N_6O_6$;
Mr=380.37;
Orthorhombic crystal system;
$P2_12_12_1$ space group;
a=5.51796(17) Å;
b=7.14615(29) Å;
c=42.9738(29) Å and
V=1694.55(14) Å$^3$.

Thus, in another aspect there is provided a polymorph A2 of Compound A having substantially equivalent peaks at a reflection angle 2-theta as shown in Table 5.

In one embodiment there is provided an isolated polymorph as defined above that is at least about 75% free of other forms.

In one embodiment there is provided an isolated polymorph as defined above that is at least about 80% free of other forms.

In one embodiment there is provided an isolated polymorph as defined above that is at least about 90% free of other forms.

In one embodiment there is provided an isolated polymorph as defined above that is at least about 95% free of other forms.

In one embodiment there is provided an isolated polymorph as defined above that is at least about 99% free of other forms.

In one embodiment there is provided an isolated polymorph as defined above that is 100% free of other forms.

In another aspect there is provided a method of obtaining the polymorph A2, the method comprising the steps of taking Compound A in a liquid vehicle and heating up to about 40 degrees for at least 9 hours.

In one embodiment the Compound A is micronized and then added to an aqueous liquid vehicle. In one embodiment Compound A is micronized into particles with sizes less than 50 microns.

In one embodiment the method includes the step of heating to about 40 degrees C. for 15 hours.

In one embodiment the liquid vehicle is adapted to provide an aqueous suspension of Compound A. In another embodiment the liquid vehicle includes a surfactant and a preservative. In one embodiment the surfactant is selected from polysorbate 80, polysorbate 60, polysorbate 40, polysorbate 20, polyoxyl 40 stearate, poloxamers, tyloxapol, POE 35 and castor oil. In one embodiment the preservative in selected from a quaternary ammonium salt, benzalkonium chloride, cetrimide, chlorobutanol, sorbic acid and boric acid.

In another aspect there is provided a pharmaceutical composition comprising polymorph A2 as defined above and further comprising one or more pharmaceutically acceptable ingredients selected from the group consisting of carriers, excipients, diluents, additives, fillers, surfactants, binders, antimicrobial preservatives, viscosity enhancing agents, and buffers.

In one embodiment the pharmaceutical composition comprising polymorph A2 defined above is formulated for ophthalmic administration.

In a further aspect, there is also provided a method of treating a subject in need of a selective adenosine $A_1$ agonist, the method comprising administering to a subject in need thereof a therapeutically effective amount of the polymorph A2 defined above.

In a further aspect, there is also provided a method of reducing intraocular pressure in a subject, the method comprising topically administering to an eye of a subject in need thereof a therapeutically effective amount of the polymorph A2 defined above.

The foregoing brief summary broadly describes the features and technical advantages of certain embodiments of the present invention. Further technical advantages will be described in the detailed description of the invention that follows. Novel features which are believed to be characteristic of the invention will be better understood from the detailed description of the invention when considered in connection with any accompanying figures and examples. However, the figures and examples provided herein are intended to help illustrate the invention or assist with developing an understanding of the invention, and are not intended to be definitions of the invention's scope.

DETAILED DESCRIPTION OF THE INVENTION

Figure 1:
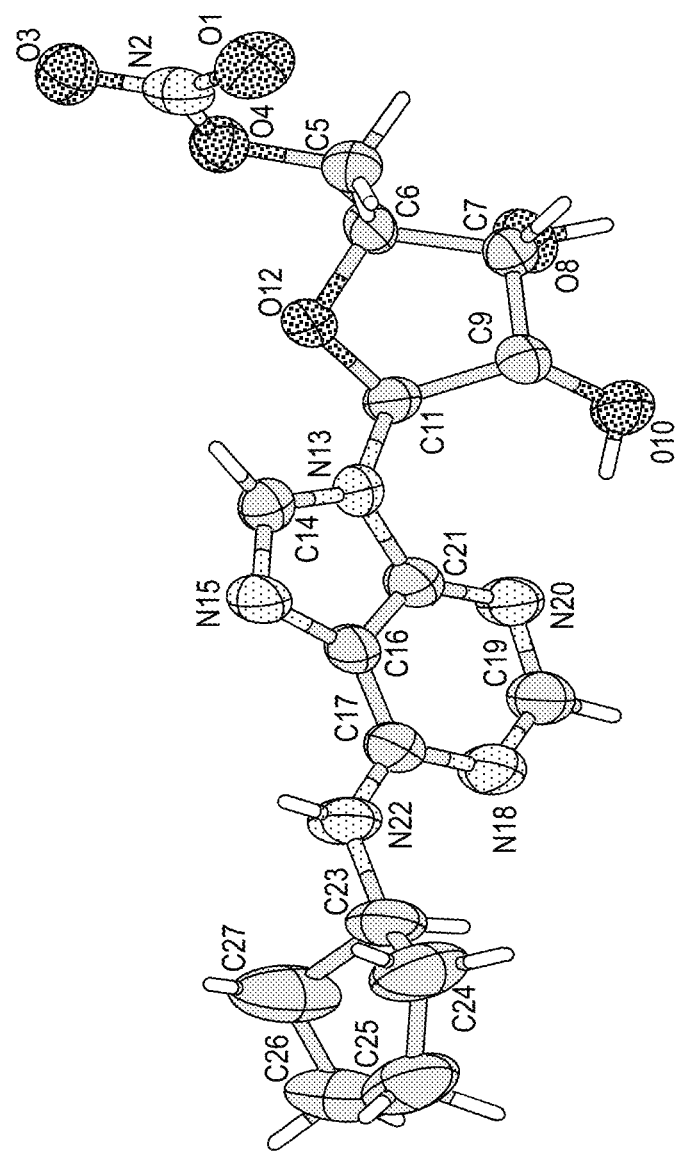
FIG. 1: shows the molecular structure and atom numbering scheme for Compound A—Form A1.

Embodiments of the present invention provide anhydrous polymorphs of Compound A.

Definitions

Some chemical structures herein are depicted using bold and dashed lines to represent chemical bonds. These bold and dashed lines depict absolute stereochemistry. A bold line indicates that a substituent is above the plane of the carbon atom to which it is attached and a dashed line indicates that a substituent is below the plane of the carbon atom to which it is attached.

The term "effective amount" as used herein refers to an amount of a selective adenosine A1 agonist that is effective for: (i) treating or preventing elevated IOP; or (ii) reducing IOP in a human.

The term "subject" is intended to include organisms, e.g., prokaryotes and eukaryotes, which are capable of suffering from or afflicted with a disease, disorder or condition associated with elevated IOP. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from an increase in IOP. In another embodiment, the subject is a cell.

The term "treat," "treated," "treating" or "treatment" includes the diminishment or alleviation of at least one symptom associated or caused by the state, disorder or disease being treated. In certain embodiments, the treatment comprises the induction of elevated IOP, followed by the activation of the compound of the invention, which would in turn diminish or alleviate at least one symptom associated or caused by the elevated IOP. For example, treatment can be diminishment of one or several symptoms of a disorder or complete eradication of a disorder.

The term "about" or "substantially" usually means within 20%, more preferably within 10%, and most preferably still within 5% of a given value or range.

Methods of Preparation and Studies

Synthesis of Compound A

The following Scheme1 shows the reaction scheme in the preparation of Compound A. The preparation of Compound A is described in detail.

The quantities detailed are calculated for a production batch of approximately 40 gms of Compound A. The production described can be scaled up.

Step 1: 1 Liter of ethanol was charged into a reactor and stirred rapidly. 0.3 kg of 6-chloroadenosine and 0.267 kg of cyclopentylamine were added to the ethanol in the reactor. The reactor was heated to reflux for 2 hr, then cooled to 8 degrees C. and kept under these conditions for 12 hours. The crystallized material was filtered from the mother liquid and the solid cake was washed with 0.33 L of ethanol to produced a wet cake. The wet cake was dried to obtain N6-cyclopentyladenosine (0.249 kg).

Step 2: Dimethoxypropane was used to protect the 2' and 3' hydroxyls on the sugar unit. 3.7 liters of acetone was charged into the reactor and was stirred rapidly. 0.249 kg of N6-cyclopentyladenosine; 0.386 kg of dimethoxypropane and 0.148 kg of p-toluenesulfonic acid were added to the acetone (3.7 L) in the reactor. The reactor was heated to 40 degrees C. for 1.5 hours. The solvents were then removed by distillation under vacuum at 40 degrees C. to prepare a dry crude material. 3.1 L of ethyl acetate were then added to the dry crude material obtained. The solution was then cooled to 6 degrees C. and 0.5N NaOH solution was added by dripping until a pH of 8 was reached. This equated to approximately 1.55 L of NaOH solution. After the phase separation was complete, 0.78 L of saturated sodium chloride 20% solution was added to the organic phase. 0.78 L of saturation sodium chloride 20% solution was added again. The two phases were stirred for 30 minutes. The organic phase that was ethyl acetate based was separated and dried with 0.157 kg of sodium sulfate and washed with 1 L of ethyl acetate. The solution was filtered and evaporated to an oil under vacuum at 55 degrees C. To the remaining oil 1.2 L of hexane and 0.3 L of ethyl acetate were added. The reaction mixture was heated to 55 degrees C. for 3 hours and then the solution was cooled to 5 degrees C. and maintained at this temperature for 12 hours. The solids were filtered and the resulting cake was washed with a 0.625 L of ethyl acetate:hexane (1:4) solution. After drying the solid 140 g of 2',3'-isopropylidene-$N^6$-cyclopentyl adenosine was obtained.

Step 3: Nitration of the 5' position of 2',3'-isopropylidene-$N^6$-cyclopentyl adenosine obtained in Step 2 was carried out with a nitric acid acetic anhydride mixture. 0.127 L of dichloromethane was charged into the reactor and stirred rapidly. 140 g of 2',3'-isopropylidene-$N^6$-cyclopentyl adenosine was added and the reaction solution was cooled to –20 degrees C. 0.547 L of a solution composed of 0.127 L nitric acid 65% in 0.420 L of acetic anhydride was added at a rate that kept the reaction mixture below –15 degrees C.—the temperature range of between –23 to –18 degrees C. has been found to be the preferred target range. If the temperature increases, then impurities were found to be generated. The addition of the acid mixture took about 0.5 hr. The mixture was stirred for 20 minutes and then quenched into 0.35 L of cold saturated sodium bicarbonate solution. The pH was corrected to 7 by the addition of solid sodium bicarbonate to the aqueous later. The organic phase was separated and the aqueous layer extracted with 0.4 L of dichloromethane. The organic phases were combined and washed with 0.6 L of saturated sodium chloride solution. The organic phase containing 2',3'-isopropylidene-$N^6$-cyclopentyladenosine-5'-nitrate was then separated for use in Step 4 below.

Step 4: Because of its lability the protected 2',3'-isopropylidene-$N^6$-cyclopentyladenosine-5'-nitrate was hydrolyzed directly without purification. The solution from Step 3 was evaporated at 20 degrees C. under vacuum to an oil. The oil was cooled to less than 2 degrees C. 1.95 L of trifluoroacetic acid:water (3:1) solution was added. The reaction mixture was stirred for 0.5 hours and allowed to warm to room temperature while being stirred. After that, the sodium bicarbonate solution was prepared and cooled to less than 10 degrees C. The sodium bicarbonate solution was added to the reaction mixture to quench the reaction. The ethyl acetate was added to the reaction vessel and the pH was adjusted and the organic layer was worked up and dried with sodium sulfate. The resulting product solution was then dried several times with magnesium sulfate and the material stripper to form crude Compound A.

The crude compound A was then recrystallized from ethanol. The crude compound A material was dissolved in ethanol then concentrated to half volume to crystallize for 36 hours. After that the resulting product was isolated by filtration to provide Compound A. $^1$H-NMR (DMSO-d$_6$): δ 1.49-1.58 (m, 4H), 1.66-1.72 (m, 2H), 1.89-1.94 (m, 2H), 4.12-4.17 (m, 1H), 4.28-4.33 (m, 1H), 4.48 (bs, 1H), 4.65-4.87 (m, 3H), 5.5 (d, J=5.1 Hz, 1H), 5.63 (d, J=5.7 Hz, 1H), 5.91 (d, J=5.1 Hz, 1H), 7.75 (d, J=7.5 Hz, 1H), 8.17 (bs, 1H), 8.30 (s, 1H); MS (ES$^+$): m/z 381.35 (M+1); Anal. Calculated for C$_{15}$H$_{20}$N$_6$O$_6$: C, 47.37; H, 5.30; N, 22.10. Found: C, 47.49; H, 5.12; N, 21.96.

Scheme 1:

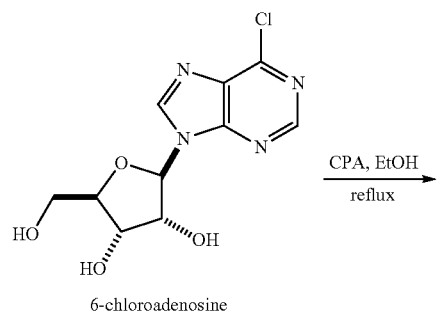

6-chloroadenosine

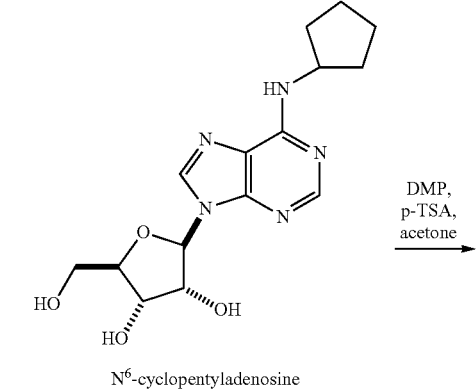

N$^6$-cyclopentyladenosine

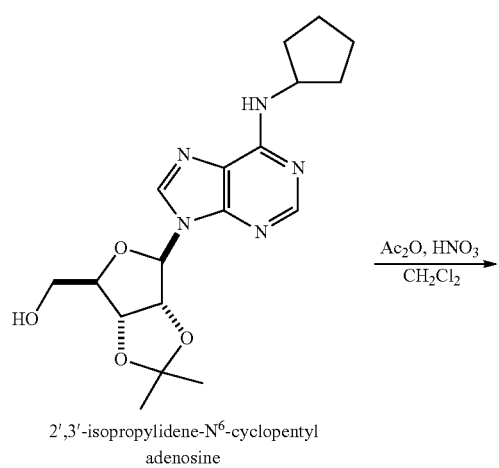

2′,3′-isopropylidene-N$^6$-cyclopentyl adenosine

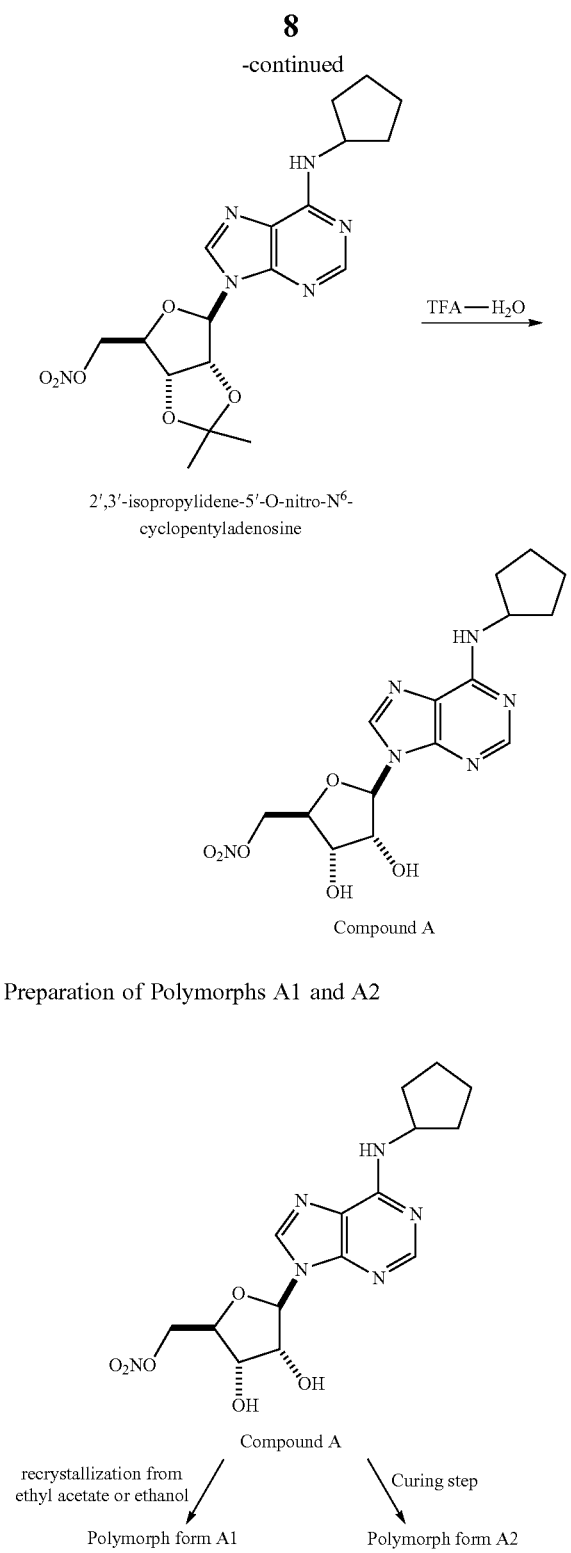

2′,3′-isopropylidene-5′-O-nitro-N$^6$-cyclopentyladenosine

Compound A

Preparation of Polymorphs A1 and A2

Compound A recrystallization from ethyl acetate or ethanol → Polymorph form A1

Curing step → Polymorph form A2

During the preparation of ophthalmic solutions of Compound A, variability was seen in particle growth size and stability. Because of the variability, efforts have been made to establish if one or more polymorphs could be isolated and purified in order to overcome the variability in particle size growth and stability.

Crystallization Study:

The Compound A material used for crystallization experiments was taken from a CMC batch prepared substantially as described in steps 1 to 4 above, which was subsequently found to comprise a mixture of approximately 67 percent of form A1 and approximately 33 percent of Form A2.

Form A1

Figure 2:
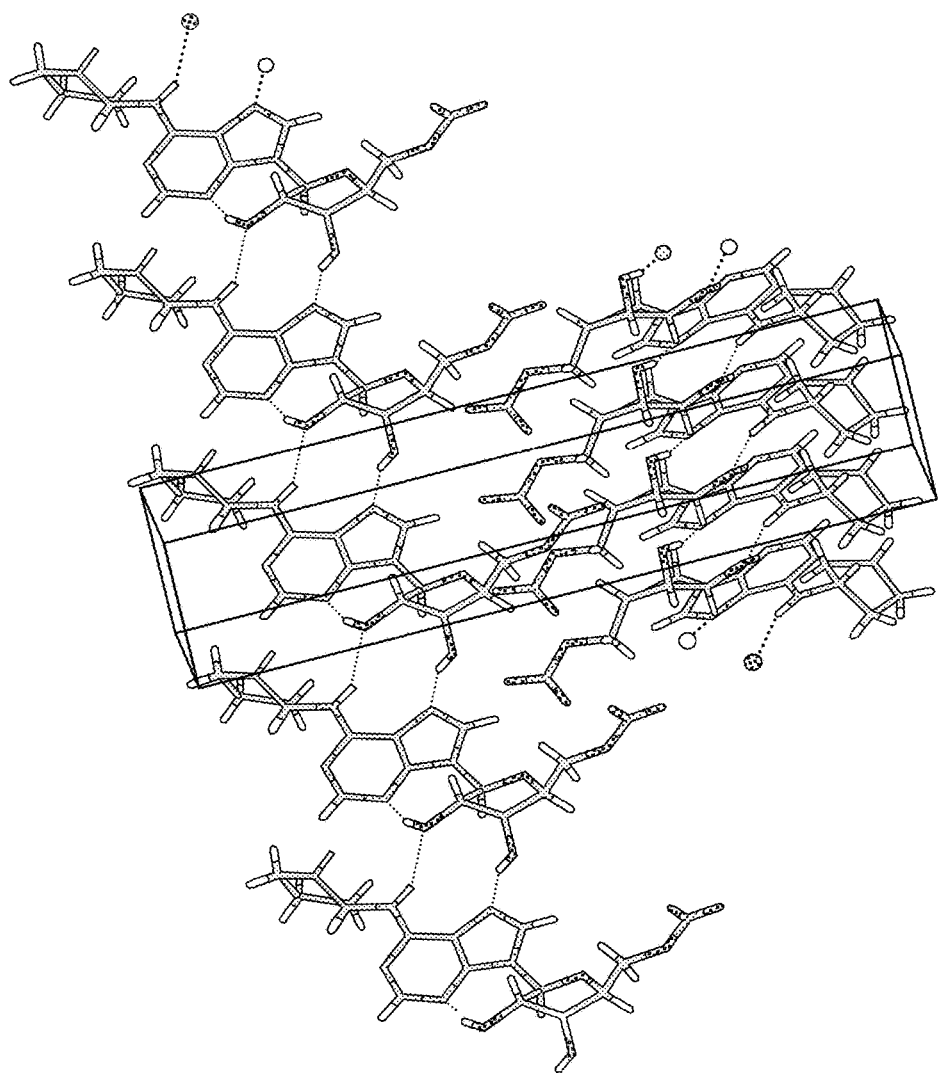
FIG. 2: shows the packing arrangement and H-bonds for Compound A—Form A1 crystals.

Several slow evaporations crystallisations as detailed in Table 1 below gave crystals using solvents ethyl acetate, isopropyl, acetate, MEK and 2-methoxyethanol that were used for establishing the crystal and molecular structure of Form A1 as shown in FIGS. 1 and 2. It has also been found that a second recrystallization from ethanol of Compound A obtained in step 4 above also yields a substantially pure form of polymorph A1. It is critical in the further recrystallization from ethanol that no moisture from the atmosphere be allowed to condense on the wet cake of compound A. This is because impurities have the potential to form in the presence of water. The preferred recrystallisation process from ethanol then dries the recrystallized compound in a freeze dryer at room temperature.

TABLE 1

Results of the slow evaporation crystallization experiments.

| Solvents | μl of solvents | Temperature | Crystals |
|---|---|---|---|
| 1,4-Dioxane | 400 | RT | Form A1 |
| MEK* | 400 | RT | Too small |
| Trifluoroethanol | 400 | RT | Too small |
| Ethyl Acetate* | 400 | RT | Form A1 |
| Isopropyl acetate* | 400 | RT | Form A1 |
| 1,2-Dimethoxyethane | 400 | RT | Glass |
| 2-Methoxyethanol | 400 | RT | Form A1 |
| 3-Methyl-2-butanone* | 400 | RT | Form A1 |
| DMF | 400 | RT | Glass |
| Iso-propanol* | 400 | RT | Too small |
| Ethanol/Water (80:20)* | 400 | RT | Too small |
| Ethanol/Water (90:10)* | 400 | RT | Too small |

*To dissolve the material, the mixture was warmed up to 60° C. and kept at this temperature for approximately 30 min. Following, it was left for crystallization at room temperature (RT).
MEK: Methylethyl ketone.
DMF: Dimethylformamide.

Approximately 3-8 mg of Compound A was placed into 8 ml vials to which 400 μL of solvent as detailed in Table 1 was added. The experiments were carried out at room temperature. Each 8 ml vial was placed in a 20 ml vial that was then closed and a small hole was pierced in the cap of the 20 ml vials. The vials were left at room temperature. A single colorless crystal (plate shaped) of approximate size 0.35×0.25×0.05 mm was directly collected from the ethyl acetate solution and mounted on a goniometer. The measurements were performed at room temperature (296K). The final crystallographic data are as shown in Table 2 below:

TABLE 2

Crystal data and Structure refinement for Compound A - Form A1

| Identification | Form A1 |
|---|---|
| Empirical Formula | $C_{15}H_{20}N_6O_6$; |
| Formula Weight | Mr = 380.37; |
| Crystal System | Monoclinic crystal system; |
| Space Group | $P2_1$ space group; |
| Unit Cell Dimensions | a = 5.546(2) Å; |
|  | b = 7.107(2) Å; |
|  | c = 21.929(9) Å; |
|  | V = 858.8(5) Å$^3$ |
| [degrees] | 96.501(8) |
| Z | 2. |
| T[K] | 296(2) |
| Å | 0.71073 |
| $D_c$ [g/cm$^3$] | 1.471 |

TABLE 2-continued

Crystal data and Structure refinement for Compound A - Form A1

| [mm$^{-1}$] | 0.115 |
|---|---|
| F(000) | 400 |
| Crystal size [mm$^3$] | 0.35 × 0.25 × 0.05 |
| Range of data collection [degrees] | 3-27.4 |
| Reflections collected | 5868 |
| Independent reflections | 3315 [$R_{int}$ = 0.0268] |
| Completeness to = 27.4 [%] | 97.8 |
| Max. and min. transmission | 0.9942 and 0.9606 |
| Data/restraints/parameters | 3315/1/289 |
| Goodness-of-fit on F$^2$ | 1.063 |
| Final R indices[I > 2(l)] | R1 = 0.0418, wR2 = 0.0970 |
| R indices (all data) | R1 = 0.0556, wR2 = 0.1050 |
| Absolute structure parameter | −0.1(12) |
| Extinction coefficient | 0.081(8) |

The single crystal measurements were performed on Nonius Kappa-CCD diffractometer equipped with Oxford Cryostream Liquid Nitrogen Cooler using MO K radiation. The data for form A1 was collected up to theta=27.5° at 296K yielding 5868 reflections. Data reduction was performed using HKL Scalepack (Otwinowski & Minor 1997) and cell parameters were obtained using Denzo and Scalepak (Otwinowski & Minor 1997) from 2569 within theta range 1 to 27.5°. The structure was solved using direct methods by SHELXZ-97 (Sheldrick, G. M. 1997a).

In addition to the single x-ray crystallography data, powder diffraction data was also collected on a D8 Advance diffractometer using CuK$_{\alpha 1}$ radiation (1.54016 Å) with germanium monochromator at Room Temperature. The data were collected from 2.5 to 32.5° theta with 0.016° theta steps on solid state LynxEye detector. The sample was measured in an 8 mm long capillary with 0.5 mm diameter.

Crystalline anhydrous polymorph form A1 is preferably characterized by a PXRD spectra having peaks at about 17.5, 20.5, 21.2, 22.7, 24.8, 33.2 and 42.1+0.2 degrees 2 theta.

In Table 3 the intensity, 2 theta and D spacing are listed together with the HKL indices. Because intensity as well as 2 theta values are dependent on the radiation used, therefore the D spacing was implemented. The radiation used was CuK$_{\alpha 1}$. 2

TABLE 3

HKL, 2 theta, D spacing and intensity from the powder diffraction of Form A1 ($P2_1$)

| h | k | l | D spacing | 2θ | Intensity |
|---|---|---|---|---|---|
| 0 | 0 | 1 | 21.757 | 4.058 | 3.070(29) |
| 0 | 0 | 2 | 10.878 | 8.121 | 1.910(36) |
| 0 | 0 | 3 | 7.252 | 12.194 | 0.623(59) |
| 0 | 1 | 1 | 6.745 | 13.115 | 0.025(65) |
| 0 | 1 | 2 | 5.943 | 14.895 | 2.323(93) |
| −1 | 0 | 1 | 5.498 | 16.109 | 3.19(30) |
| 1 | 0 | 0 | 5.480 | 16.162 | 6.84(33) |
| 0 | 0 | 4 | 5.439 | 16.283 | 0.91(15) |
| −1 | 0 | 2 | 5.192 | 17.064 | 1.06(15) |
| 1 | 0 | 1 | 5.147 | 17.214 | 4.07(16) |
| 0 | 1 | 3 | 5.072 | 17.472 | 11.87(17) |
| −1 | 0 | 3 | 4.697 | 18.878 | 0.92(18) |
| 1 | 0 | 2 | 4.642 | 19.104 | 16.40(23) |
| 0 | 0 | 5 | 4.351 | 20.393 | 0.5(17) |
| 1 | −1 | −1 | 4.346 | 20.420 | 20.7(26) |
| 1 | 1 | 0 | 4.337 | 20.462 | 19.5(15) |
| 0 | 1 | 4 | 4.317 | 20.559 | 10.14(40) |
| 1 | −1 | −2 | 4.190 | 21.187 | 42.01(46) |
| 1 | 1 | 1 | 4.166 | 21.309 | 7.14(92) |
| −1 | 0 | 4 | 4.160 | 21.342 | 1.29(81) |
| 1 | 0 | 3 | 4.106 | 21.624 | 1.29(24) |

TABLE 3-continued

HKL, 2 theta, D spacing and intensity from the powder diffraction of Form A1 (P2$_1$)

| h | k | l | D spacing | 2θ | Intensity |
|---|---|---|-----------|-----|-----------|
| 1 | −1 | −3 | 3.916 | 22.686 | 77.44(52) |
| 1 | 1 | 2 | 3.884 | 22.876 | 12.02(34) |
| 0 | 1 | 5 | 3.709 | 23.971 | 2.41(28) |
| −1 | 0 | 5 | 3.664 | 24.270 | 0.03(28) |
| 0 | 0 | 6 | 3.626 | 24.530 | 1.18(60) |
| 1 | 0 | 4 | 3.617 | 24.590 | 5.78(63) |
| 1 | −1 | −4 | 3.589 | 24.791 | 22.15(38) |
| 1 | 1 | 3 | 3.554 | 25.035 | 5.20(97) |
| 0 | 2 | 0 | 3.547 | 25.082 | 14.93(93) |
| 0 | 2 | 1 | 3.501 | 25.419 | 9.96(33) |
| 0 | 2 | 2 | 3.373 | 26.405 | 0.01(32) |
| 1 | −1 | −5 | 3.256 | 27.371 | 1.19(38) |
| −1 | 0 | 6 | 3.238 | 27.525 | 0.76(70) |
| 0 | 1 | 6 | 3.229 | 27.604 | 2.8(13) |
| 1 | 1 | 4 | 3.223 | 27.658 | 12.60(99) |
| 1 | 0 | 5 | 3.198 | 27.873 | 0.26(46) |
| 0 | 2 | 3 | 3.187 | 27.977 | 0.30(44) |
| 0 | 0 | 7 | 3.108 | 28.699 | 0.65(36) |
| 1 | −2 | −1 | 2.981 | 29.953 | 14.3(20) |
| 1 | 2 | 0 | 2.978 | 29.982 | 0.2(25) |
| 0 | 2 | 4 | 2.971 | 30.050 | 5.21(90) |
| 1 | −1 | −6 | 2.946 | 30.318 | 7.63(44) |
| 1 | −2 | −2 | 2.929 | 30.494 | 1.64(66) |
| 1 | 2 | 1 | 2.921 | 30.581 | 0.0(11) |
| 1 | 1 | 5 | 2.916 | 30.638 | 2.36(86) |
| −1 | 0 | 7 | 2.881 | 31.021 | 5.24(41) |
| 1 | 0 | 6 | 2.848 | 31.390 | 2.6(62) |
| 0 | 1 | 7 | 2.847 | 31.397 | 0.1(62) |
| 1 | −2 | −3 | 2.831 | 31.580 | 11.04(53) |
| 1 | 2 | 2 | 2.819 | 31.720 | 3.23(48) |
| −2 | 0 | 1 | 2.766 | 32.335 | 1.54(44) |
| 0 | 2 | 5 | 2.750 | 32.539 | 4.6(62) |
| −2 | 0 | 2 | 2.749 | 32.548 | 1.3(64) |
| 2 | 0 | 0 | 2.740 | 32.657 | 1.45(63) |
| 0 | 0 | 8 | 2.720 | 32.908 | 0.37(43) |
| 1 | −2 | −4 | 2.699 | 33.163 | 18.54(59) |
| −2 | 0 | 3 | 2.689 | 33.286 | 0.53(97) |
| 1 | 2 | 3 | 2.684 | 33.350 | 0.65(92) |
| 2 | 0 | 1 | 2.673 | 33.500 | 2.6(11) |
| 1 | −1 | −7 | 2.669 | 33.550 | 0.12(97) |
| 1 | 1 | 6 | 2.643 | 33.894 | 0.46(44) |
| −2 | 0 | 4 | 2.596 | 34.521 | 1.31(47) |
| −1 | 0 | 8 | 2.583 | 34.701 | 0.04(83) |
| 2 | −1 | −1 | 2.577 | 34.778 | 1.6(15) |
| 2 | 0 | 2 | 2.574 | 34.832 | 0.3(12) |
| 2 | −1 | −2 | 2.563 | 34.978 | 1.06(92) |
| 2 | 1 | 0 | 2.556 | 35.081 | 0(15) |
| 1 | 0 | 7 | 2.556 | 35.086 | 3(15) |
| 1 | −2 | −5 | 2.549 | 35.182 | 9.2(11) |
| 0 | 1 | 8 | 2.539 | 35.316 | 2.7(16) |
| 0 | 2 | 6 | 2.536 | 35.369 | 2.3(26) |
| 1 | 2 | 4 | 2.533 | 35.412 | 4.6(16) |
| 2 | −1 | −3 | 2.515 | 35.673 | 7.10(49) |
| 2 | 1 | 1 | 2.501 | 35.874 | 0.56(48) |
| −2 | 0 | 5 | 2.479 | 36.208 | 0.01(47) |
| 2 | 1 | 5 | 2.089 | 43.279 | 5.9(61) |
| 1 | −2 | −8 | 2.088 | 43.295 | 0.3(65) |
| 2 | 2 | 2 | 2.083 | 43.403 | 2.0(33) |
| 0 | 1 | 10 | 2.080 | 43.471 | 2(110) |
| −2 | 0 | 8 | 2.080 | 43.474 | 1(120) |
| 0 | 3 | 5 | 2.078 | 43.519 | 0.7(59) |
| 1 | 2 | 7 | 2.074 | 43.615 | 9.8(13) |
| 1 | −3 | −4 | 2.056 | 44.008 | 9.4(15) |
| 2 | 0 | 6 | 2.053 | 44.070 | 0.0(17) |
| 1 | 3 | 3 | 2.049 | 44.156 | 2.0(11) |
| 1 | −1 | −10 | 2.036 | 44.452 | 5.63(92) |
| 2 | −2 | −5 | 2.032 | 44.555 | 7.3(10) |
| 1 | 1 | 9 | 2.019 | 44.850 | 2.3(18) |
| 2 | 2 | 3 | 2.018 | 44.889 | 0.0(21) |
| 0 | 2 | 9 | 1.998 | 45.362 | 0(670) |
| 2 | −1 | −8 | 1.996 | 45.403 | 70(970) |

Form A2

None of the crystallization trials or techniques attempted, including (i) slow evaporation of solvent, (ii) vapor diffusion of non polar solvent into liquid solution of Compound A and (iii) polar solvent and temperature controlled crystallization with slow cooling rate; yielded suitable crystals of Form A2 for single crystal analysis. In some experiments, such as, for example, in the temperature controlled crystallizations using various mixtures of ethanol/water, very thin needles were obtained. In most of the cases the crystals seemed to be twinned crystals, however none of these crystals gave enough reflections to obtain proper cell parameters. These crystals were however used to attempt X-ray powder diffraction. Therefore the X-ray Powder Diffraction Pattern (XRPD) was obtained and attempts were then made for solving the structure of the Form A2 from the powder data. The first step was to obtain the proper unit cell. After several trials, two possible cell settings were obtained. Both were orthorhombic although with different Bravais face centering. One of these cells was a face centred cell C, while the other was primitive P. Based on the fact that the cell C could be transformed into a smaller one, namely P, the latter was refined and attempts to solve the structure with this configuration setting were made. Also, with the P cell the asymmetric unit was reduced to 1 molecule with C it concerned 2 symmetry independent molecules. For the cell refinement the Pawley fit was used. A Pawley fit based on the high resolution X-ray diffraction pattern was used to check the purity of the sample. The main purpose of the Pawley fit is to refine cell parameters from the complete pattern. In the Pawley method, profiles are analytical, their width is constrained to follow a Caglioti law with the three refinable parameters U, V, W as defined in most of the Rietveld-derived software. The software used for calculation in this project was Topas with following criteria of fit:

$Y_{o,m}$ and $Y_{c,m}$ are the observed and calculated data, respectively at data point m.

M the number of data points,

P the number of parameters, $W_m$ the weighting given to data point m which for counting statistics is given by $w_m = 1/\sigma(Y_{o,m})^2$ where $\sigma(Y_{o,m})$ is the error in $Y_{o,m}$ $$R_{exp} = \sqrt{\frac{M-P}{\sum w_m Y_{o,m}^2}} \; ; \; R_{wp} = \sqrt{\frac{\sum w_m (Y_{o,m} - Y_{c,m})^2}{\sum w_m Y_{o,m}^2}} \; ;$$

$$R_p = \sqrt{\frac{\sum |Y_{o,m} - Y_{c,m}|}{\sum Y_{o,m}}}$$

$$GOF = chi^2 = \frac{R_{wp}}{R_{exp}} = \sqrt{\frac{\sum w_m (Y_{o,m} - Y_{c,m})^2}{M-P}}$$

TABLE 4

Parameters of the Pawley fit for Compound A - Form A2

| Identification | Form A2 |
|---|---|
| T[K] | 293(2) |
| Å | 1.54056 |
| Crystal System | Orthorhombic crystal system; |
| Space Group | P2$_1$2$_1$2$_1$ space group; |
| Unit Cell Dimensions | a = 5.51796(17) Å; |
| | b = 7.14615(29) Å; |
| | c = 42.9738(29) Å; |
| | V = 1694.55(14) Å³ |
| Capillary size | 0.5 × 0.8 |
| Range for data collection | 2-22.5 |
| R$_{exp}$ | 1.52 |
| R$_{wp}$ | 2.64 |

TABLE 4-continued

Parameters of the Pawley fit for Compound A - Form A2

| | |
|---|---|
| Rp | 1.91 |
| R$_{Bragg}$ | 7.8 |
| GOF | 1.74 |

Figure 3:
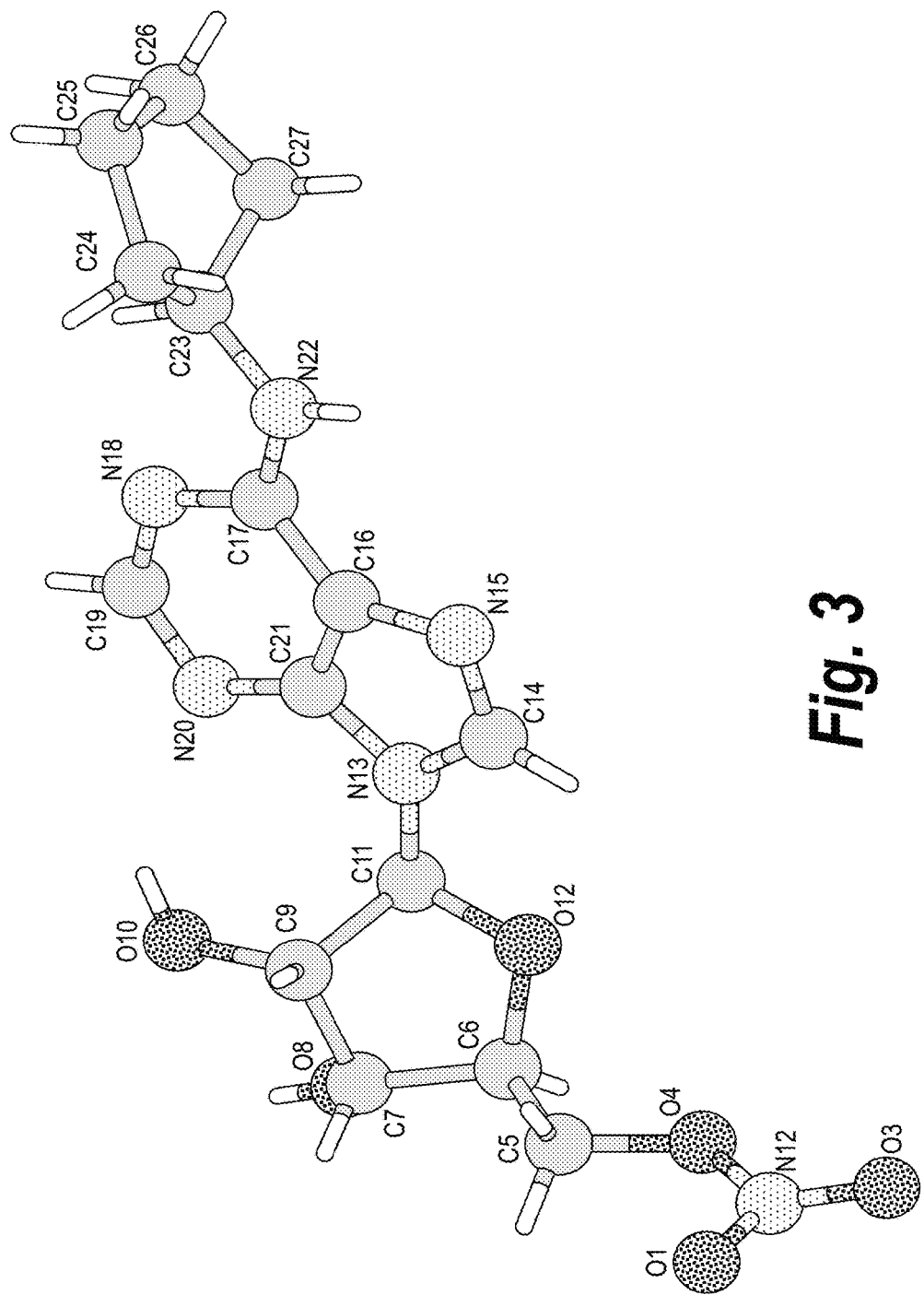
FIG. 3: shows the molecular structure and atom numbering scheme for Compound A—Form A2
Figure 4:
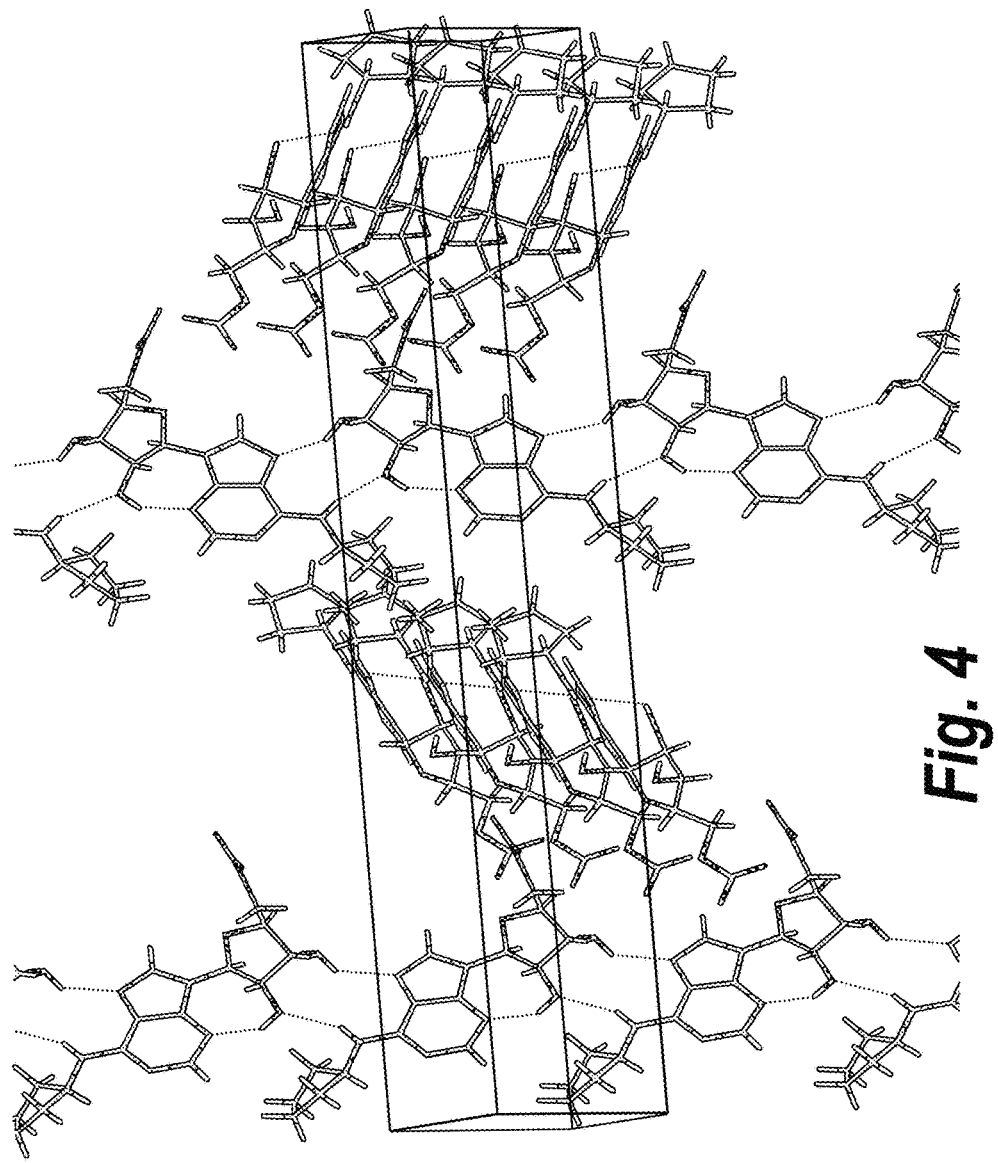
FIG. 4: shows the packing arrangement and H-bonds for Compound A—Form A2 crystals.
Figure 5:
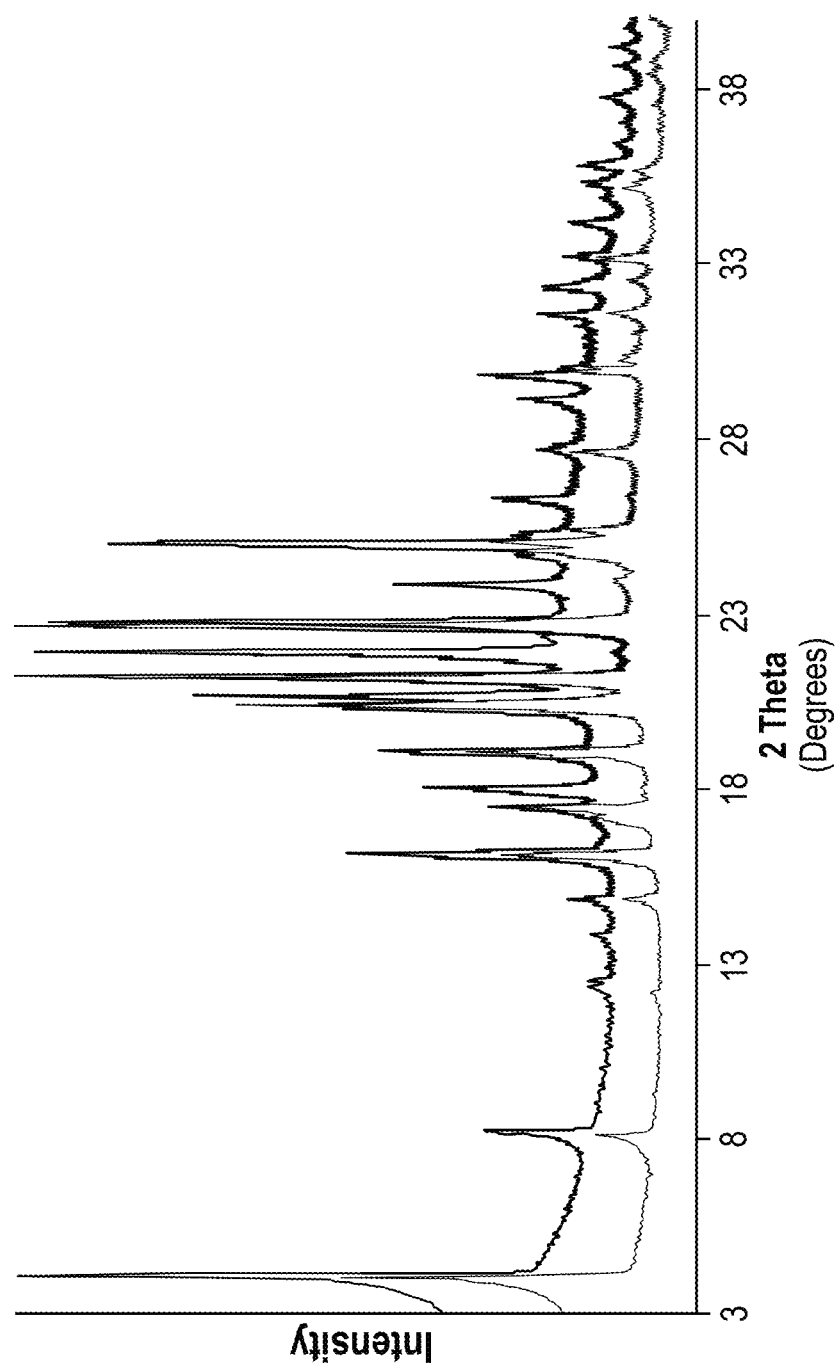
FIG. 5: shows an overlay in the x-ray powder spectra observed for the forms of Compound A described herein. The lower gray line represents the A1 form and the upper black line represents the form A2.
Figure 6:
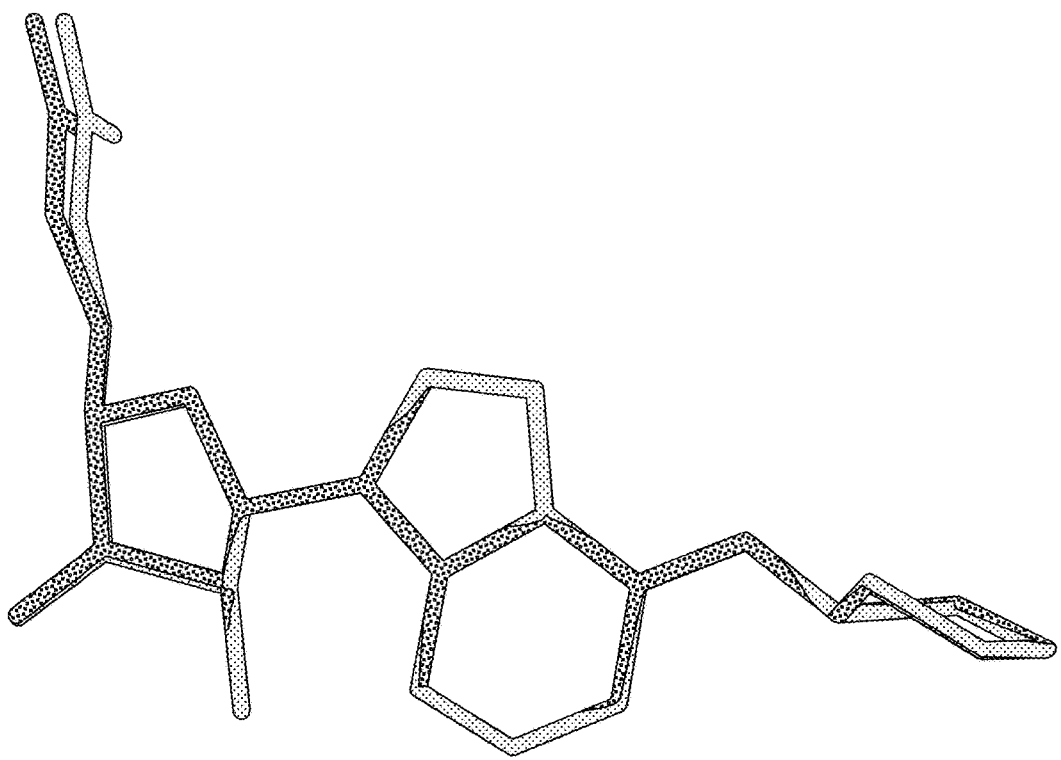
FIG. 6: shows the superposition of molecules of Form A1 (black) and Form A2 (grey)

For the structure solution, the Topas 3.0 software was employed (Bruker-AXS, 2005) using simulated annealing method. The model was built on the Z-matrix and several torsion angles were set as free variables. The obtained model was not refined except for the unit cell. The H-atoms were included based on geometry and H-Bond scheme. FIG. 3 shows the molecular structure of Form 2 of Compound A and FIG. 4 shows the crystal packing and the H-bond scheme.

XRPD patterns were obtained using a high-throughput XRPD set-up. The plates were mounted on a Bruker GADDS diffractometer equipped with a Hi-Star area detector. The XRPD platform was calibrated using Silver Behenate for the long d-spacings and Corundum for the short d-spacings.

Data collection was carried out at room temperature using monochromatic CuKα radiation in the 2-theta region between 1.5 degrees and 41.5 degrees, which is the most distinctive part of the XRPD pattern between the polymorph forms. The diffraction pattern of each well was collected in 2 theta ranges (1.5 degrees≤2 theta≤21.5 degrees for the first frame, and 19.5 degrees≤2 theta≤41.5 degrees for the second) with an exposure time of 30 seconds for each frame. No background subtraction or curve smoothing was applied to the XRPD patterns. The carrier material used during XRPD analysis was transparent to X-rays and contributed only slightly to the background.

Crystalline anhydrous polymorph form A2 is preferably characterized by PXRD spectra having peaks at about 16.9, 18.1, 19.1, 20.8, 21.3, 22.0, 22.8, 23.8, 24.9, 25.0, 29.1, 29.8, 34.2 and 35.8+0.2 degrees 2 theta.

In Table 5 the intensity, 2 theta and D spacing are listed together with the HKL indices. Because intensity as well as 2 theta values are dependent on the radiation used, therefore the D spacing was implemented. The radiation used was CuK$_{α1}$.

TABLE 5

HKL, 2 theta, D spacing and intensity from the powder diffraction of Form A2 (P2$_1$2$_1$2$_1$)

| h | k | l | D spacing | 2θ | Intensity |
|---|---|---|---|---|---|
| 0 | 0 | 2 | 21.487 | 4.109 | 3.341(28) |
| 0 | 0 | 4 | 10.743 | 8.223 | 2.277(38) |
| 0 | 0 | 6 | 7.162 | 12.348 | 0.690(57) |
| 0 | 1 | 1 | 7.049 | 12.547 | 0.802(58) |
| 0 | 1 | 2 | 6.781 | 13.045 | 0.032(57) |
| 0 | 1 | 3 | 6.395 | 13.837 | 1.088(68) |
| 0 | 1 | 4 | 5.950 | 14.877 | 2.330(82) |
| 0 | 1 | 5 | 5.495 | 16.117 | 2.50(22) |
| 1 | 0 | 1 | 5.473 | 16.182 | 16.69(24) |
| 0 | 0 | 8 | 5.372 | 16.489 | 0.31(12) |
| 1 | 0 | 2 | 5.345 | 16.574 | 0.02(12) |
| 1 | 0 | 3 | 5.149 | 17.207 | 0.78(11) |
| 0 | 1 | 6 | 5.059 | 17.517 | 9.55(14) |
| 1 | 0 | 4 | 4.908 | 18.058 | 15.49(17) |
| 0 | 1 | 7 | 4.657 | 19.043 | 2.50(33) |
| 1 | 0 | 5 | 4.643 | 19.098 | 18.42(35) |
| 1 | 0 | 6 | 4.371 | 20.300 | 0.0(12) |
| 1 | 1 | 0 | 4.367 | 20.317 | 14.0(13) |
| 1 | 1 | 1 | 4.345 | 20.423 | 21.46(33) |
| 0 | 0 | 10 | 4.297 | 20.652 | 4.4(20) |
| 0 | 1 | 8 | 4.294 | 20.669 | 14.2(23) |
| 1 | 1 | 2 | 4.280 | 20.737 | 34.73(53) |
| 1 | 1 | 3 | 4.178 | 21.251 | 62.18(36) |
| 1 | 0 | 7 | 4.104 | 21.637 | 3.26(21) |
| 1 | 1 | 4 | 4.046 | 21.951 | 64.81(39) |
| 0 | 1 | 9 | 3.970 | 22.375 | 3.18(21) |
| 1 | 1 | 5 | 3.894 | 22.821 | 67.15(41) |
| 1 | 0 | 8 | 3.849 | 23.089 | 0.02(22) |
| 1 | 1 | 6 | 3.729 | 23.844 | 23.77(31) |
| 0 | 1 | 10 | 3.683 | 24.147 | 1.11(24) |
| 1 | 0 | 9 | 3.611 | 24.636 | 5.44(27) |
| 0 | 0 | 12 | 3.581 | 24.843 | 1.32(64) |
| 0 | 2 | 0 | 3.573 | 24.900 | 0.0(10) |
| 0 | 2 | 1 | 3.561 | 24.987 | 16.0(37) |
| 1 | 1 | 7 | 3.559 | 25.001 | 57.11(34) |
| 0 | 2 | 2 | 3.525 | 25.247 | 7.78(28) |
| 0 | 2 | 3 | 3.467 | 25.675 | 0.11(25) |
| 0 | 1 | 11 | 3.428 | 25.972 | 0.02(26) |
| 0 | 2 | 4 | 3.390 | 26.264 | 0(1200) |
| 1 | 0 | 10 | 3.390 | 26.264 | 0(1200) |
| 1 | 1 | 8 | 3.389 | 26.278 | 13(11) |
| 0 | 2 | 5 | 3.299 | 27.003 | 0.24(27) |
| 1 | 1 | 9 | 3.223 | 27.658 | 6.71(31) |
| 0 | 1 | 12 | 3.202 | 27.843 | 4.61(77) |
| 0 | 2 | 6 | 3.197 | 27.882 | 0.02(89) |
| 1 | 0 | 11 | 3.188 | 27.961 | 0.02(42) |
| 0 | 2 | 7 | 3.088 | 28.889 | 3.68(33) |
| 0 | 0 | 14 | 3.070 | 29.067 | 0.02(57) |
| 1 | 1 | 10 | 3.063 | 29.129 | 13.39(58) |
| 1 | 0 | 12 | 3.004 | 29.716 | 0.3(17) |
| 0 | 1 | 13 | 3.000 | 29.754 | 0.3(90) |
| 1 | 2 | 0 | 2.999 | 29.765 | 4.9(81) |
| 1 | 2 | 1 | 2.992 | 29.839 | 23.29(88) |
| 0 | 2 | 8 | 2.975 | 30.012 | 0.81(68) |
| 1 | 2 | 2 | 2.970 | 30.060 | 4.79(66) |
| 1 | 2 | 3 | 2.936 | 30.426 | 0.16(34) |
| 1 | 1 | 11 | 2.912 | 30.680 | 1.09(34) |
| 1 | 2 | 4 | 2.889 | 30.931 | 2.18(35) |
| 0 | 2 | 9 | 2.861 | 31.241 | 3.31(36) |
| 1 | 0 | 13 | 2.836 | 31.524 | 2.60(83) |
| 1 | 2 | 5 | 2.832 | 31.569 | 13.87(87) |
| 0 | 1 | 14 | 2.820 | 31.700 | 0.94(41) |
| 1 | 1 | 12 | 2.769 | 32.301 | 1.3(12) |
| 1 | 2 | 6 | 2.766 | 32.335 | 12.9(14) |
| 2 | 0 | 0 | 2.759 | 32.425 | 2.17(88) |
| 2 | 0 | 1 | 2.753 | 32.493 | 3.93(89) |
| 0 | 2 | 10 | 2.747 | 32.564 | 2.65(63) |
| 2 | 0 | 2 | 2.737 | 32.698 | 1.03(41) |
| 2 | 0 | 3 | 2.709 | 33.037 | 0.47(39) |
| 1 | 2 | 7 | 2.695 | 33.219 | 13.32(50) |
| 0 | 0 | 16 | 2.686 | 33.333 | 0.44(92) |
| 1 | 0 | 14 | 2.682 | 33.376 | 0.02(88) |
| 2 | 0 | 4 | 2.672 | 33.507 | 1.62(43) |
| 0 | 1 | 15 | 2.659 | 33.677 | 0.31(39) |
| 0 | 2 | 11 | 2.637 | 33.974 | 0.0(33) |
| 1 | 1 | 13 | 2.636 | 33.985 | 1.5(34) |
| 2 | 0 | 5 | 2.627 | 34.103 | 3.97(60) |
| 1 | 2 | 8 | 2.619 | 34.214 | 14.87(53) |
| 2 | 0 | 6 | 2.575 | 34.818 | 0.3(46) |
| 2 | 1 | 0 | 2.574 | 34.829 | 2.2(52) |
| 2 | 1 | 1 | 2.569 | 34.893 | 4.43(92) |
| 2 | 1 | 2 | 2.556 | 35.086 | 4.65(43) |
| 1 | 0 | 15 | 2.543 | 35.270 | 0.0(11) |
| 1 | 2 | 9 | 2.540 | 35.312 | 11.6(13) |
| 2 | 1 | 3 | 2.533 | 35.405 | 0.15(98) |
| 0 | 2 | 12 | 2.529 | 35.461 | 5.87(80) |
| 2 | 0 | 7 | 2.517 | 35.648 | 0.0(15) |
| 0 | 1 | 16 | 2.514 | 35.683 | 0.0(25) |
| 1 | 1 | 14 | 2.511 | 35.724 | 2.5(15) |
| 2 | 1 | 4 | 2.503 | 35.847 | 15.03(56) |
| 2 | 1 | 5 | 2.466 | 36.409 | 3.57(54) |
| 1 | 2 | 10 | 2.459 | 36.504 | 1.95(65) |
| 2 | 0 | 8 | 2.454 | 36.585 | 0.02(56) |
| 0 | 2 | 13 | 2.427 | 37.018 | 2.26(64) |

TABLE 5-continued

HKL, 2 theta, D spacing and intensity from
the powder diffraction of Form A2 ($P2_12_12_1$)

| h | k | l | D spacing | 2θ | Intensity |
|---|---|---|---|---|---|
| 2 | 1 | 6 | 2.422 | 37.086 | 1.62(68) |
| 1 | 0 | 16 | 2.415 | 37.201 | 1.13(49) |
| 1 | 1 | 15 | 2.396 | 37.514 | 2.28(58) |
| 2 | 0 | 9 | 2.389 | 37.623 | 4.3(25) |
| 0 | 0 | 18 | 2.387 | 37.646 | 0.0(30) |
| 0 | 1 | 17 | 2.383 | 37.716 | 0.6(17) |
| 1 | 2 | 11 | 2.379 | 37.785 | 8.3(82) |
| 0 | 3 | 1 | 2.378 | 37.795 | 2.2(80) |
| 2 | 1 | 7 | 2.374 | 37.873 | 2.95(98) |
| 0 | 3 | 2 | 2.368 | 37.974 | 1.72(55) |
| 0 | 3 | 3 | 2.350 | 38.273 | 0.02(46) |
| 0 | 2 | 14 | 2.328 | 38.639 | 6.6(11) |
| 0 | 3 | 4 | 2.326 | 38.687 | 2.9(18) |
| 2 | 0 | 10 | 2.322 | 38.754 | 0.9(66) |
| 2 | 1 | 8 | 2.321 | 38.764 | 1.8(59) |
| 1 | 2 | 12 | 2.299 | 39.146 | 1.3(32) |
| 1 | 0 | 17 | 2.298 | 39.167 | 0.0(43) |
| 0 | 3 | 5 | 2.296 | 39.214 | 11.8(17) |
| 1 | 1 | 16 | 2.288 | 39.351 | 2.64(54) |
| 2 | 1 | 9 | 2.266 | 39.753 | 5.2(23) |
| 0 | 1 | 18 | 2.264 | 33.775 | 0.0(26) |
| 0 | 3 | 6 | 2.260 | 39.850 | 1.52(90) |
| 2 | 0 | 11 | 2.254 | 39.973 | 4.10(57) |
| 0 | 2 | 15 | 2.235 | 40.318 | 1.37(55) |
| 1 | 2 | 13 | 2.221 | 40.582 | 0.5(43) |
| 0 | 3 | 7 | 2.221 | 40.591 | 4.1(43) |
| 2 | 1 | 10 | 2.208 | 40.835 | 0.02(60) |
| 1 | 0 | 18 | 2.191 | 41.165 | 0.0(15) |
| 1 | 1 | 17 | 2.188 | 41.230 | 3(14) |
| 1 | 3 | 0 | 2.187 | 41.246 | 1(25) |
| 2 | 0 | 12 | 2.186 | 41.274 | 2(24) |
| 1 | 3 | 1 | 2.184 | 41.302 | 6(49) |
| 2 | 2 | 0 | 2.184 | 41.310 | 0(40) |
| 2 | 2 | 1 | 2.181 | 41.366 | 8.8(38) |
| 0 | 3 | 8 | 2.178 | 41.433 | 2.1(33) |
| 1 | 3 | 2 | 2.176 | 41.469 | 11.6(29) |
| 2 | 2 | 2 | 2.173 | 41.533 | 2.8(12) |
| 1 | 3 | 3 | 2.162 | 41.747 | 11.1(12) |
| 2 | 2 | 3 | 2.159 | 41.810 | 7.1(18) |
| 0 | 1 | 19 | 2.156 | 41.860 | 2.7(15) |
| 2 | 1 | 11 | 2.149 | 42.003 | 5.0(99) |
| 0 | 0 | 20 | 2.149 | 42.016 | 0(14) |
| 0 | 2 | 16 | 2.147 | 42.052 | 0.9(81) |
| 1 | 2 | 14 | 2.145 | 42.087 | 2.4(56) |
| 1 | 3 | 4 | 2.143 | 42.132 | 3.6(29) |
| 2 | 2 | 4 | 2.140 | 42.195 | 6.3(12) |
| 0 | 3 | 9 | 2.132 | 42.370 | 5.30(72) |
| 1 | 3 | 5 | 2.119 | 42.624 | 2.3(32) |
| 2 | 0 | 13 | 2.118 | 42.651 | 0.2(49) |
| 2 | 2 | 5 | 2.116 | 42.686 | 6.8(25) |
| 1 | 1 | 18 | 2.095 | 43.148 | 1.4(22) |
| 1 | 0 | 19 | 2.093 | 43.194 | 0.2(81) |
| 1 | 3 | 6 | 2.092 | 43.219 | 3(11) |
| 2 | 1 | 12 | 2.090 | 43.254 | 6.0(89) |
| 2 | 2 | 6 | 2.089 | 43.280 | 2.5(44) |
| 0 | 3 | 10 | 2.083 | 43.398 | 0.10(84) |
| 1 | 2 | 15 | 2.072 | 43.657 | 6.91(88) |
| 0 | 2 | 17 | 2.064 | 43.835 | 0.0(11) |
| 1 | 3 | 7 | 2.060 | 43.913 | 5.9(22) |
| 0 | 1 | 20 | 2.058 | 43.968 | 4(18) |
| 2 | 2 | 7 | 2.057 | 43.974 | 0(17) |
| 2 | 0 | 14 | 2.052 | 44.098 | 0.99(86) |
| 0 | 3 | 11 | 2.034 | 44.512 | 1.2(11) |
| 2 | 1 | 13 | 2.031 | 44.581 | 6.0(12) |
| 1 | 3 | 8 | 2.026 | 44.704 | 10.2(16) |
| 2 | 2 | 8 | 2.023 | 44.764 | 8.8(23) |
| 1 | 1 | 19 | 2.008 | 45.105 | 0(38) |
| 1 | 0 | 20 | 2.002 | 45.252 | 0(2700) |
| 1 | 2 | 16 | 2.001 | 45.286 | 0(4300) |

Controlling the Formation of the Form of Polymorph

It has been found that the formation of the particular polymorphic form can be controlled. As described above the Form A1 can be obtained predominantly via recrystallization from ethanol or under slow evaporation conditions.

Figure 7:
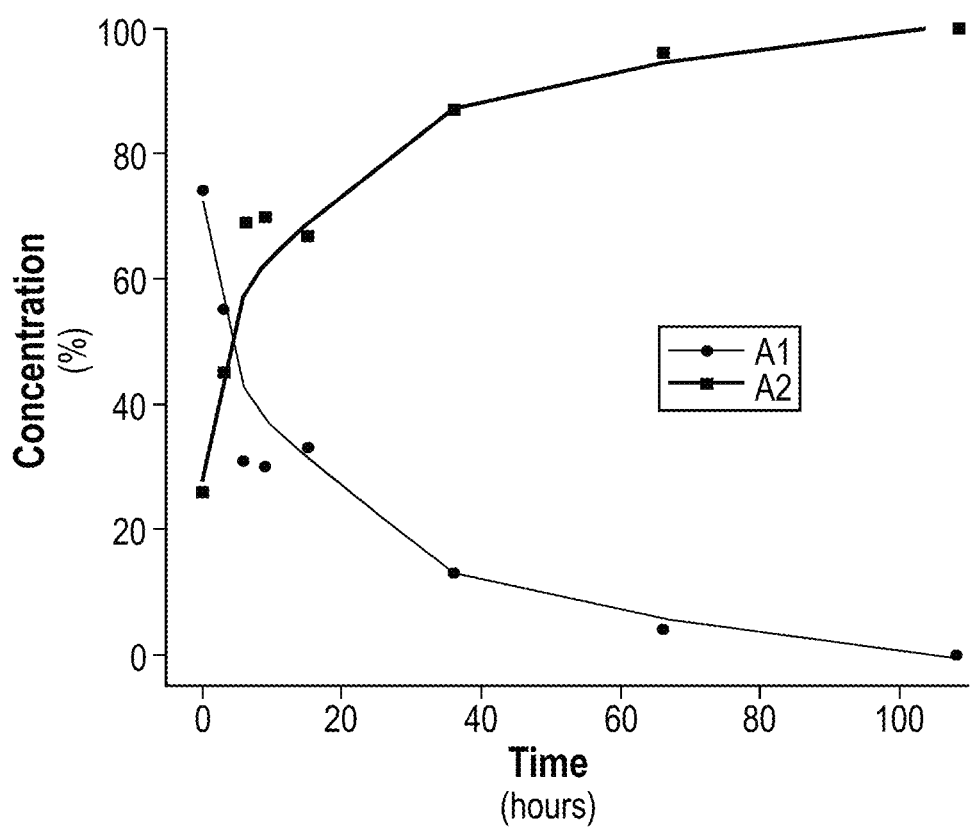
FIG. 7: shows the XRPD data plot of conversion of polymorph form A1 to polymorph form A2 over time at 40 degrees C.

It has also been established that ripening or curing of Compound A particles suspended in an aqueous suspension formulated for ocular delivery at 40 degrees C. for a relatively short period of time formed polymorph form A2 from polymorph form A1. The aqueous suspension samples were kept at 40 degrees C. for up to 108 hours and monitored by particle size measurement, XRPD and microphotography. Particle size measurements showed that average sizes increased significantly over 15 hours. Thereafter, sizes remained effectively constant to 108 hours. XRPD analyses indicated a change in polymorph content from about 74% A1 to 26% A2 at time zero to 0% A1 to 100% A2 at 108 hours at 40 degrees C. FIG. 7 shows the conversion of form A1 to A2 over time. Also, habit changes coupled with A2 growth were reflected in the XRPD patterns and could be monitored by a difference in selected peak intensities from planes within the crystal lattice perpendicular to the c axis that change in intensity as the habit of the crystal changes. The intensity differences changed up to 9 hours and remained constant thereafter indicating that the habit changes were completed during this time. Microphotographs showed blade or plate-like crystal habits of particles in suspension.

When the aqueous suspension ocular formulation containing Compound A in the A1 polymorph is stored at 2-8° C., a temperature required to limit decomposition of Compound A over long term storage, the habit of the suspended particles changes slowly over a period of 6 to 12 months. During this time the small irregular particles of suspended drug change to rod-like habits, with many particles having a length along the longest dimension over 100 microns. These changes make it much more difficult to resuspend Compound A particles by sonication and shaking in order to form a homogeneous suspension for dosing.

The conversion of the A1 form to the A2 form has been found to limit any further changes to particle habit, size or polymorph content when the aqueous suspension, which is suitable for ocular delivery of the drug, is stored over a 6 month period at either 5° C. or 25° C. Also, the cured aqueous suspension is more easily resuspended by shaking, a favourable characteristic for suspension formulations for ocular drug delivery.

The particle size analyses were performed on a Cilas 1180 Particle Size Analyzer. The parameters used were liquid mode, sample refractive index=1.62 (determined using Cargille immersion oils), liquid refractive index=1.333 (value for water), 30 second measurement, 180 rpm stirring, 120 rpm pump circulation, no sonication, 5 repeat measurements.

Formulation Example

A batch of sterile material of Compound A was prepared as described above under the "Synthesis of Compound A". The resulting Compound A material was then sterilized with gamma irradiation at up to 40 kGray and then formulated into the following aqueous formulations:

Aqueous Formulation

| Ingredient | %, W/V |
|---|---|
| Compound A | 0.152-0.76 |
| Sodium CMC | 0.7 |
| Benzalkonium Chloride | 0.01 |

-continued

| Ingredient | %, W/V |
|---|---|
| Polysorbate 80 | 0.3 |
| Citric Acid Monohydrate | 0.152 (7 mM) |
| NaOH/HCl | pH 5.1 ± 0.1 |
| NaCl | q.s. to 270-330 mOsm |
| Purified Water | q.s. to 100.00 |

Various concentrations of Compound A formulation lots were prepared from 0.152, 0.30, 0.61, 0.91, 2.42, 0.46, 0.76%, W/V to provide for the ability to deliver different levels of Compound A per drop of formulation. For example one drop of the 0.152%, W/V of compound A would deliver 50 mcg per drop, 0.30%, W/V would deliver 100 mcg per drop, right through to 0.76% W/V delivering 250 mcg per drop. The formulation lots were then heated to undergo the curing step and convert the A1 polymorph form of Compound A to the A2 polymorph form of Compound A. The curing step was undertaken by placing the formulation lots at 40 degrees C. for 48 hours and then reverting the formulations lots to the desired longer term storage conditions for stability studies.

Two of the formulation lots, namely 0.46% W/V of Compound A and a 0.76% W/V were studied for long term stability and particle size growth at 5 degrees Celsius and 25 degrees Celsius for 6 months. Two of the formulation lots, namely 0.46% W/V of Compound A and a 0.76% W/V were studied for long term stability and particle size growth at 5 degrees Celsius for 18 months. The results are tabulated below in Table 6.

TABLE 6

| Formulation | Time (months) | Impurities | pH | Particle Size Distribution (microns) |
|---|---|---|---|---|
| 0.46% at 5° C. | 0 | 1% | 5.1 | $X_{10} = 1.746$ $X_{50} = 6.992$ $X_{90} = 14.087$ |
| 0.46% at 5° C. | 1 | 1% | 5.0 | $X_{10} = 0.907$ $X_{50} = 6.285$ $X_{90} = 13.485$ |
| 0.46% at 5° C. | 3 | 1% | 5.0 | $X_{10} = 1.792$ $X_{50} = 7.082$ $X_{90} = 14.356$ |
| 0.46% at 5° C. | 6 | 1% | 5.1 | $X_{10} = 1.777$ $X_{50} = 6.939$ $X_{90} = 13.698$ |
| 0.46% at 5° C. | 12 | 1% | 5.1 | $X_{10} = 1.398$ $X_{50} = 6.679$ $X_{90} = 13.396$ |
| 0.46% at 5° C. | 18 | 1% | 5.1 | $X_{10} = 1.666$ $X_{50} = 6.882$ $X_{90} = 13.074$ |
| 0.46% at 25° C. | 0 | 1% | 5.1 | $X_{10} = 1.746$ $X_{50} = 6.416$ $X_{90} = 13.698$ |
| 0.46% at 25° C./60% RH | 1 | 1% | 5.0 | $X_{10} = 1.036$ $X_{50} = 6.416$ $X_{90} = 13.698$ |
| 0.46% at 25° C./60% RH | 3 | 3% | 5.1 | $X_{10} = 1.656$ $X_{50} = 6.705$ $X_{90} = 12.805$ |
| 0.46% at 25° C./60% RH | 6 | 4% | 5.0 | $X_{10} = 1.809$ $X_{50} = 6.741$ $X_{90} = 12.380$ |
| 0.76% at 5° C. | 0 | 1% | 5.1 | $X_{10} = 1.524$ $X_{50} = 6.773$ $X_{90} = 12.778$ |
| 0.76% at 5° C. | 1 | 1% | 5.1 | $X_{10} = 1.115$ $X_{50} = 6.456$ $X_{90} = 12.944$ |
| 0.76% at 5° C. | 3 | 1% | 5.1 | $X_{10} = 1.455$ $X_{50} = 6.745$ $X_{90} = 13.104$ |
| 0.76% at 5° C. | 6 | 1% | 5.1 | $X_{10} = 1.541$ $X_{50} = 6.638$ $X_{90} = 11.833$ |
| 0.76% at 5° C. | 12 | 1% | 5.1 | $X_{10} = 1.407$ $X_{50} = 6.635$ $X_{90} = 12.314$ |
| 0.76% at 5° C. | 18 | 1% | 5.1 | $X_{10} = 1.611$ $X_{50} = 6.840$ $X_{90} = 12.672$ |
| 0.76% at 25° C./60% RH | 0 | 1% | 5.1 | $X_{10} = 1.524$ $X_{50} = 6.773$ $X_{90} = 12.778$ |
| 0.76% at 25° C./60% RH | 1 | 1% | 5.1 | $X_{10} = 1.056$ $X_{50} = 6.107$ $X_{90} = 11.551$ |
| 0.76% at 25° C./60% RH | 3 | 2% | 5.1 | $X_{10} = 1.446$ $X_{50} = 6.691$ $X_{90} = 12.724$ |
| 0.76% at 25° C./60% RH | 6 | 3% | 5.1 | $X_{10} = 1.619$ $X_{50} = 6.292$ $X_{90} = 10.240$ |

It can be seen from the results in Table 6 that the particle size distributions of the two formulation lots are stable over the time under the conditions tested. The results also show that the levels of impurities and pH remain stable for the formulations at 5 degrees Celsius over 18 months, while there is a slow increase in the impurities for the formulations held at 25 degrees Celsius over 6 months.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein can be utilized according to such related embodiments of the present invention. Thus, the following claims are intended to encompass within their scope modifications, substitutions, and variations to processes, manufactures, compositions of matter, compounds, means, methods, and/or steps disclosed herein.

The invention claimed is:

1. An aqueous pharmaceutical composition formulated for ophthalmic administration comprising a suspension of polymorph A2 of compound A, [2R,3S,4R,5R)-5-(6-(cyclopentylamino)-9H-purin-9-yl)-3,4-dihydroxytetrahydrofuran-2-yl)]methyl nitrate:

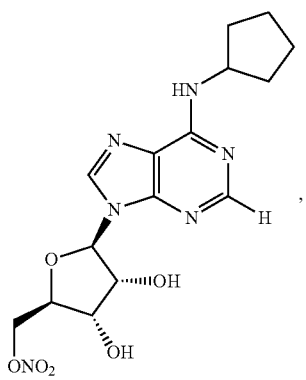

having the following crystal data, $C_{15}H_{20}N_6O_6$;

Mr=380.37;

Orthorhombic crystal system;

$P2_12_12_1$ space group;

a=5.51796(17) Å;

b=7.14615(29) Å;

c=42.9738(29) Å and

V=1694.55(14) Å$^3$;

a surfactant and a preservative, wherein the aqueous pharmaceutical composition is at least about 75% free of other polymorphic forms of compound A.

2. The aqueous pharmaceutical composition of claim 1 that is at least about 80% free of other solid forms of compound A.

3. The aqueous pharmaceutical composition of claim 1 that is at least about 90% free of other solid forms of compound A.

4. The aqueous pharmaceutical composition of claim 1 that is at least about 95% free of other solid forms of compound A.

5. The aqueous pharmaceutical composition of claim 1 that is at least about 99% free of other solid forms of compound A.

6. The aqueous pharmaceutical composition of claim 1 that is 100% free of other solid forms of compound A.

7. The aqueous pharmaceutical composition of claim 1, wherein the surfactant is selected from the group consisting of polysorbate 80, polysorbate 60, polysorbate 40, polysorbate 20, polyoxyl 40 stearate, poloxamers, tyloxapol, polyolester (POE) 35 and castor oil.

8. The aqueous pharmaceutical composition of claim 1, wherein the preservative in selected from a quaternary ammonium salt, benzalkonium chloride, cetrimide, chlorobutanol, sorbic acid and boric acid.

9. The aqueous pharmaceutical composition of claim 1, further comprising one or more pharmaceutically acceptable ingredients selected from the group consisting of carriers, excipients, diluents, additives, viscosity enhancing agents, and buffers.

10. The aqueous pharmaceutical composition of claim 1, comprising compound A at a concentration selected from the group consisting of 0.152, 0.3, 0.46, 0.61, 0.76, 0.91, and 2.42% W/V.

11. The aqueous pharmaceutical composition of claim 1, comprising compound A at a concentration of 0.152-0.76% W/V.

12. The aqueous pharmaceutical composition of claim 11, wherein compound A comprises an $X_{90}$ particle size distribution of about 10.240-14.356 microns.

13. The aqueous pharmaceutical composition of claim 12, wherein compound A comprises an $X_{50}$ particle size distribution of about 6.285-7.082 microns in diameter.

14. The aqueous pharmaceutical composition of claim 13, wherein compound A comprises an $X_{10}$ particle size distribution of about 0.907-1.809.

15. The aqueous pharmaceutical composition of claim 1, wherein the formulation comprises 0.46% W/V compound A.

16. The aqueous pharmaceutical composition of claim 15, wherein the composition remains stable at 5° C. for 18 months.

17. The aqueous pharmaceutical composition of claim 1, wherein the formulation comprises 0.76% W/V compound A.

18. The aqueous pharmaceutical composition of claim 17, wherein the composition remains stable at 5° C. for 18 months.

* * * * *